(12) United States Patent
Arnold

(10) Patent No.: US 8,087,254 B2
(45) Date of Patent: Jan. 3, 2012

(54) PERSONAL HEAT CONTROL DEVICE AND METHOD

(75) Inventor: Anthony Peter Arnold, Boulder, CO (US)

(73) Assignee: Its Kool, LLC, Boulder, CO (US)

( * ) Notice: Subject to any disclaimer, the term of this patent is extended or adjusted under 35 U.S.C. 154(b) by 808 days.

(21) Appl. No.: 11/815,911

(22) PCT Filed: Feb. 10, 2006

(86) PCT No.: PCT/US2006/004708
§ 371 (c)(1),
(2), (4) Date: Aug. 9, 2007

(87) PCT Pub. No.: WO2006/086618
PCT Pub. Date: Aug. 17, 2006

(65) Prior Publication Data
US 2008/0141681 A1    Jun. 19, 2008

Related U.S. Application Data

(63) Continuation-in-part of application No. 11/056,559, filed on Feb. 10, 2005, now abandoned.

(60) Provisional application No. 60/543,783, filed on Feb. 10, 2004.

(51) Int. Cl.
*F25B 21/02*    (2006.01)
(52) U.S. Cl. .................. 62/3.5; 62/3.2; 62/3.7
(58) Field of Classification Search .............. 62/3.2, 62/3.5, 3.7
See application file for complete search history.

(56) References Cited

U.S. PATENT DOCUMENTS

| | | | |
|---|---|---|---|
| 2,798,494 | A | 7/1957 | Sukacev |
| 2,938,356 | A | 5/1960 | McMahon |
| 3,099,137 | A | 7/1963 | Jamison |
| 3,132,688 | A | 5/1964 | Nowak |

(Continued)

FOREIGN PATENT DOCUMENTS

WO    8400480 A1    2/1984

(Continued)

OTHER PUBLICATIONS

International Search Report and Written Opinion for PCT Application No. PCT/US2006/004708, mailed Jul. 20, 2006.

(Continued)

*Primary Examiner* — Cheryl J Tyler
*Assistant Examiner* — Jonathan Koagel
(74) *Attorney, Agent, or Firm* — Faegre & Benson LLP

(57) ABSTRACT

Embodiments of the present invention provide a device for personal heat control, including a flexible housing comprising a cooling surface, a heating surface thermally insulated from the cooling surface, and a heat transfer unit configured to transfer heat from cooling surface to heating surface. Other embodiments of the present invention provide a system for cooling wearers of impact-resistant helmets, including an impact-resistant outer shell, foam pads affixed to an inside of the impact-resistant outer shell and configured to rest on a wearer's head, thermoelectric cooling devices spaced to avoid interference with foam pads and configured to rest against the head, a heat sink, and heat pipes thermally coupled at one end to thermoelectric cooling devices and at another end to the heat sink, and configured to transfer heat from thermoelectric cooling devices to heat sink with minimal heat loss, the heat pipes spaced to avoid interference with the foam pads.

21 Claims, 19 Drawing Sheets

U.S. PATENT DOCUMENTS

| | | | | |
|---|---|---|---|---|
| 3,554,815 A * | 1/1971 | Osborn | | 136/203 |
| 4,172,495 A * | 10/1979 | Zebuhr et al. | | 165/46 |
| 4,470,263 A * | 9/1984 | Lehovec et al. | | 62/3.5 |
| 4,483,021 A * | 11/1984 | McCall | | 2/7 |
| 4,860,748 A | 8/1989 | Chiurco et al. | | |
| 5,150,583 A * | 9/1992 | Jaster et al. | | 62/179 |
| 5,197,294 A * | 3/1993 | Galvan et al. | | 62/3.62 |
| 5,269,369 A * | 12/1993 | Faghri | | 607/104 |
| 5,562,604 A | 10/1996 | Yablon et al. | | |
| 5,603,728 A | 2/1997 | Pachys | | |
| 5,800,490 A | 9/1998 | Patz et al. | | |
| 5,802,865 A | 9/1998 | Strauss | | |
| 5,890,371 A * | 4/1999 | Rajasubramanian et al. | | 62/259.2 |
| 5,970,718 A | 10/1999 | Arnold | | |
| 6,023,932 A | 2/2000 | Johnston | | |
| 6,125,636 A * | 10/2000 | Taylor et al. | | 62/3.5 |
| 6,183,855 B1 * | 2/2001 | Buckley | | 428/317.9 |
| 6,438,964 B1 | 8/2002 | Giblin | | |
| 6,840,955 B2 * | 1/2005 | Ein | | 607/108 |
| 2002/0124574 A1 | 9/2002 | Guttman et al. | | |
| 2004/0211189 A1 | 10/2004 | Arnold | | |
| 2005/0193742 A1 | 9/2005 | Arnold | | |

FOREIGN PATENT DOCUMENTS

| | | |
|---|---|---|
| WO | 2005010444 A1 | 2/2005 |
| WO | 2006086618 A1 | 8/2006 |

OTHER PUBLICATIONS

International Search Report and Written Opinion for PCT Application No. PCT/US2004/023124, mailed Nov. 15, 2004.

"AGV Cooled & Heated Motorcycle Helmet-XL-BSR," Apr. 2, 2004, http:egi.ebay.com/ebaymotors/ws/eBayISAPI.dll?View&Item-2465393868.

Air Safe Inc., "Cool Zone Cooling Product," 2004, www.airsafeusa.com.

Buist, Richard J. et al., Cool-Power, Inc., "The Thermoelectrically Cooled Helmet," pp. 88-94, Plano, Texas, date unknown.

Buist, Richard J. et al., "TE Techonology, Inc., Theoretical Analysis of Thermoelectric Cooling Performance Enhancement via Thermal and Electrical Pulsing," 4 pages, Traverse City, Michigan, date unknown.

Frean, Alexandra, "Safety Helmets May Not Be Giving Cricketers a Head Start," British Psychological Society Conference, Times Online, Apr. 15, 2004.

Hall, Celia, "Cricket Hemets May Slow the Brain, Says Study," the Sunday Telegraph Magazine, Apr. 15, 2004.

Ritzer, Todd M. et al., "A Critical Evaluation of Today's Thermoelectric Modules," 16th International Conference on Thermoelectrics, 1997, pp. 619-623, Traverse City, Michigan.

TE Technology, Inc. "Download Publications," 5 pages, 2003, www.tetech.com, downloaded Aug. 13, 2004 from http://www.tetech.com/publications/.

* cited by examiner

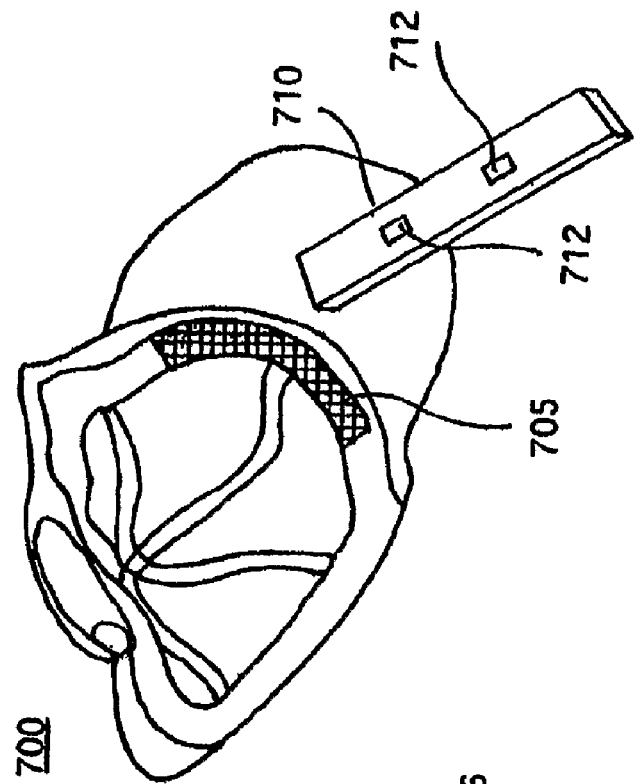
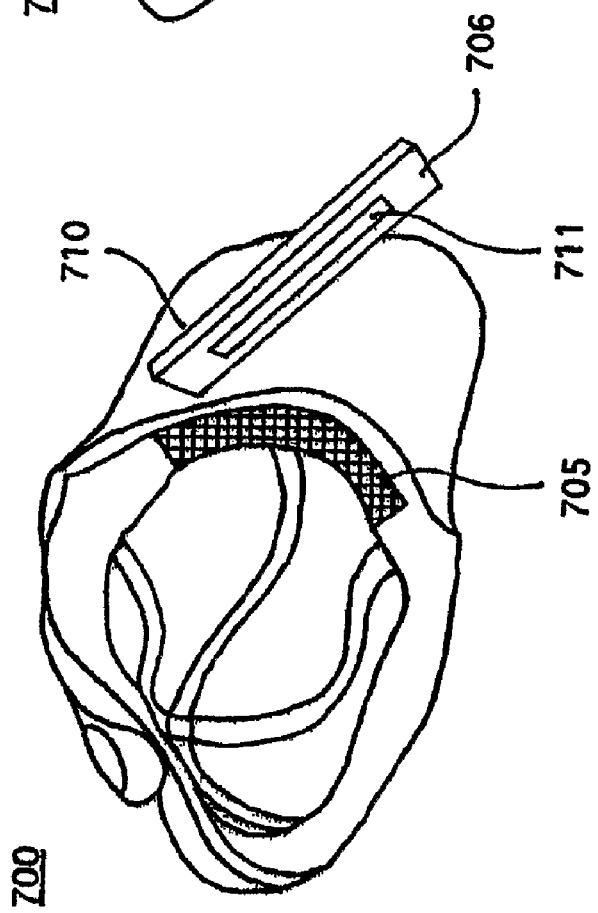
Figure 7A
Figure 7B

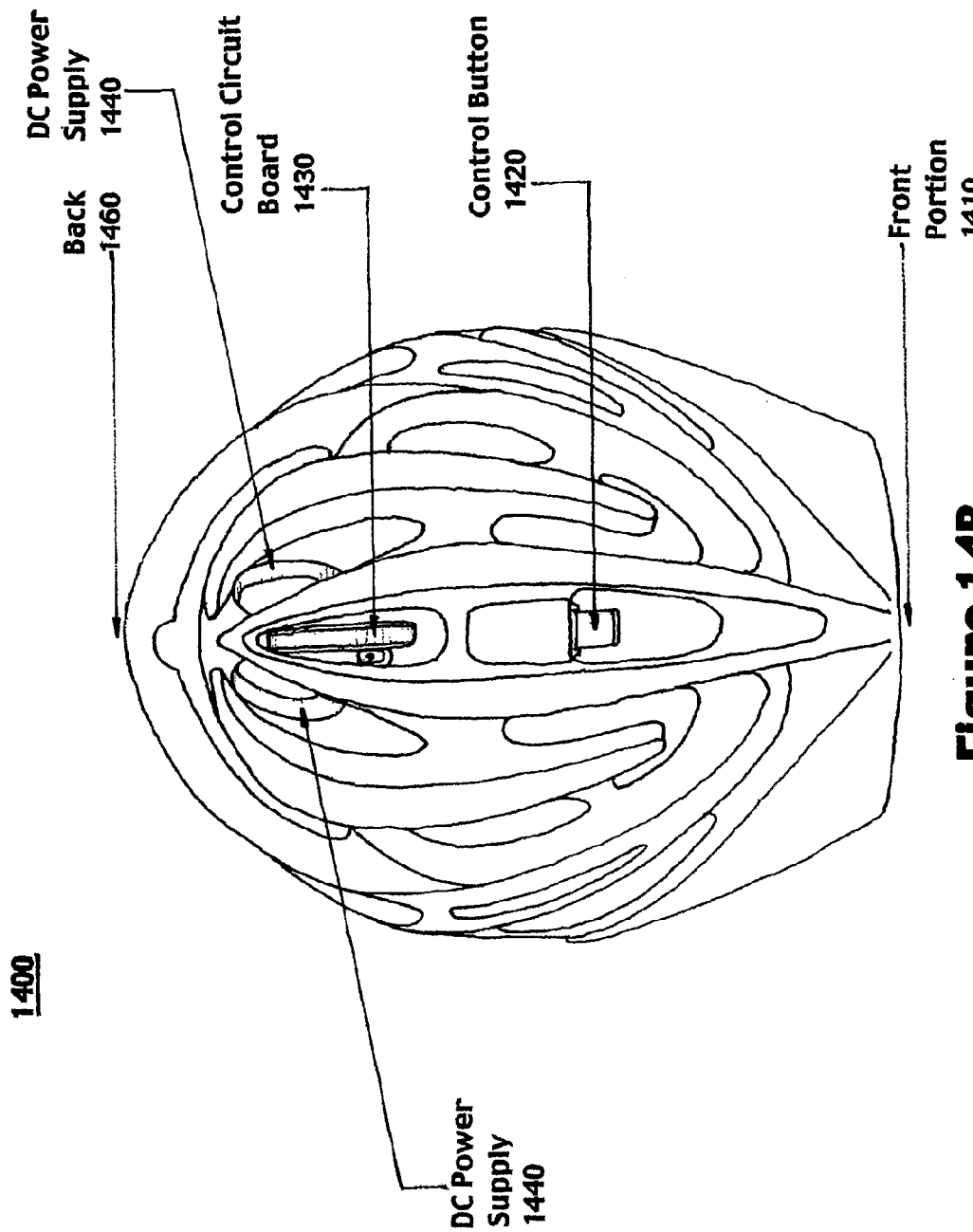

PERSONAL HEAT CONTROL DEVICE AND METHOD

CROSS-REFERENCE TO RELATED APPLICATIONS

The present application is a continuation-in-part of U.S. patent application Ser. No. 11/056,559, entitled, "Personal Heat Control Device and Method," and filed on Feb. 10, 2005 now abandoned, which claims the benefit of U.S. Provisional Patent Application No. 60/543,783, entitled "Personal Heat Control Device and Method" and filed on Feb. 10, 2004. The aforementioned applications are incorporated by reference herein in their entirety for all purposes.

BACKGROUND

1. Field

Embodiments of the present invention relate generally to personal heat control. More particularly, embodiments of the present invention relate to personal heat control devices that may be stand-alone, dedicated devices, integrated into or temporarily affixed or attached to other conventional devices, integrated into or temporarily affixed or attached to articles of clothing, or otherwise conveniently worn on a person to achieve cooling or heating of the person's body.

2. Description of Related Art

In a hot or cold environment, it is often desirable to have access to convenient, personalized heat control to improve personal comfort in such an environment. For example, placing a cool item against the skin of a person who is staying in a hot environment tends to alleviate the person's discomfort due to the high temperature.

SUMMARY

Methods and apparatus for personal heat control are described. According to one embodiment of the present invention, a portable heat control device is integrated within a garment. The portable heat control device may be self-contained or the components may be distributed at various locations of the garment. The portable heat control device includes an optional flexible enclosure, a cooling surface, a heating surface, and a heat transfer unit. The heating surface is thermally insulated from the cooling surface. The heat transfer unit is accommodated in or on the flexible enclosure and is configured and disposed to cool the cooling surface and heat the heating surface.

According to one embodiment, the flexible enclosure is configured to accommodate an internal DC power supply. In an alternative embodiment, DC power may be supplied via one or more distributed units located within or which have been otherwise incorporated with or attached to the garment.

According to one embodiment, the flexible enclosure is configured to accommodate a control circuit board including a tinier. In an alternative embodiment, the control circuit board may be communicatively coupled via wire or wireless means with the portable heat control device and reside external to the flexible enclosure as one or more distributed units located within or which have been otherwise incorporated with or attached to the garment.

In this manner, the garment becomes the attachment mechanism for maintaining the proximity of the portable heat control device to the user's body and the support structure for containing or holding various distributed components of a portable heat control device.

Other features of embodiments of the present invention will be apparent from the accompanying drawings and from the detailed description that follows.

BRIEF DESCRIPTION OF THE SEVERAL VIEWS OF THE DRAWINGS

Embodiments of the present invention are illustrated by way of example, and not by way of limitation, in the figures of the accompanying drawings and in which like reference numerals refer to similar elements and in which:

FIGS. 7A and 7B depict a flexible personal heat-control device which may be incorporated within or removably attached to a baseball cap according to one embodiment of the present invention.

FIGS. 14A-B depict the inside and outside, respectively, of a cycling helmet having incorporated therein a distributed personal cooling device (PCD) according to one embodiment of the present invention.

DETAILED DESCRIPTION

Figure 1A:
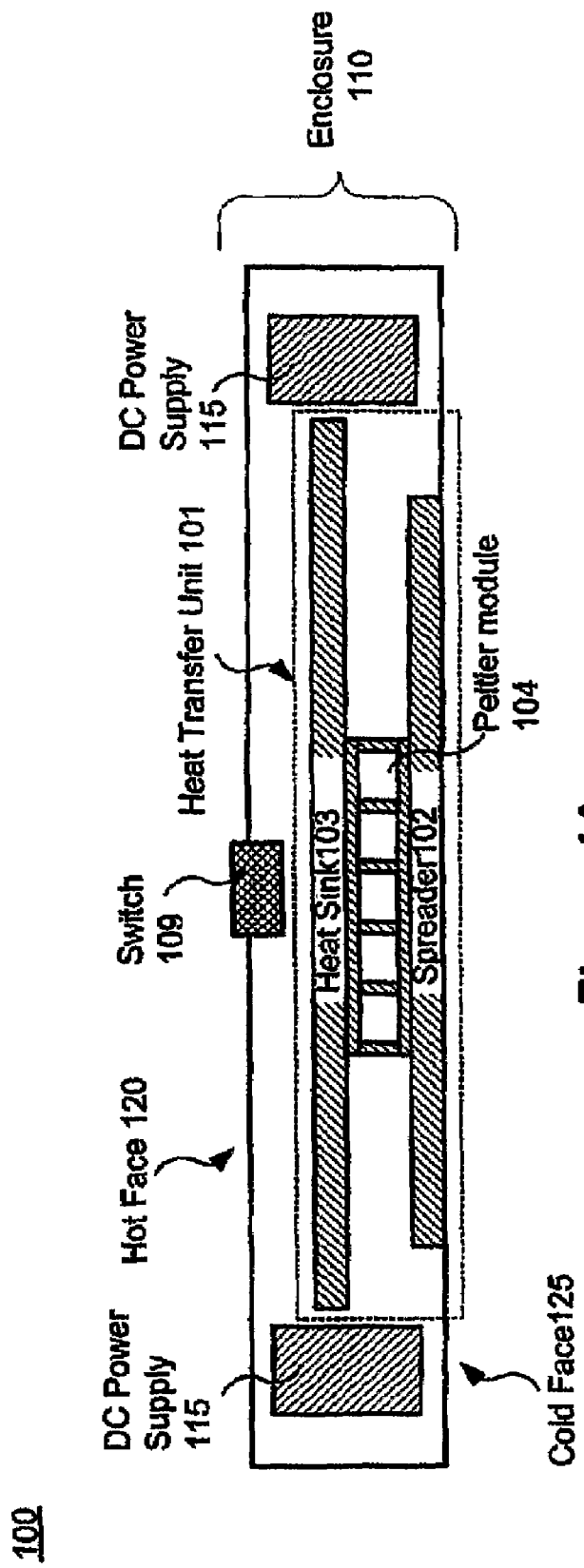
FIG. 1A depicts an illustrative cross-sectional side view of a personal heat-control device constructed as a flexible strip according to one embodiment of the present invention.

Methods and apparatus for personal heat control are described. Broadly stated, a personal heat control device includes a heat transfer unit, such as a thermoelectric cooling (TEC) module employing a phenomenon known as the "Peltier Effect," for providing cooling and heating. According to one embodiment, a TEC module is mounted in or on a flexible enclosure that is either wearable by a person or removably attachable or integrated into to a wearable item such as an article of clothing, athletic gear, safety or protective gear, or accessories.

According to another embodiment, a personal heat-control device may be a stand-alone device or integrated within an accessory or other conventional portable device, such as a key FOB, pendant, mobile phone, pager, personal digital assistant, camera, spectacles, hearing aids, jewelry. The portable device whether integrated or stand-alone enables heat transfer to be made from or to a person's body for comfort or refreshment purposes by directly or indirectly engaging a heating surface or a cooling surface of the device with, for example, the palm of ones hand, the inside of the wrist, the forehead, the temple, or other area of the body where blood vessels are close to the skin surface. In this manner, rapid and effective transfer of heat for cooling or warming the body can be achieved. Additionally, according to various embodiments of the present invention, the cooling or warming can be achieved with economical expenditure of electrical energy and under close control. Miniature personal heat-control devices, such as PCDs, bring a new dimension to personal cooling in the fields of leisure, fashion, military, firefighting, construction, industry, healthcare and sport; and eliminate or reduce the need for fans, ice crystals, water sprays and bulky collar coolers.

A more general description of personal heat control device using a TEC module has been given in the U.S. Pat. No. 5,970,718, entitled "PERSONAL HEAT CONTROL" and issued to the present inventor. U.S. Pat. No. 5,970,718 is hereby incorporated herein by reference.

Terminology

Brief definitions of terms used throughout this application are given below.

The terms "connected" or "coupled" and related terms are used in an operational sense and are not necessarily limited to a direct connection or coupling. The term "thermally coupled" means coupled in a way capable of conducting heat, and the term "thermally insulated" means separated by a substance that deters heat transfer.

The term "flexible" generally means bendable and adaptable under relatively little force. In the context of various embodiments of the present invention, flexible is intended to describe the dynamic conforming nature of the personal heat-control device to the general shape of a portion of a person's body, such as wrist, ankle, neck, shoulder, back, chest, forehead, rib cage, arch, temple, palm, etc., directly or indirectly in contact with or otherwise engaging a surface of the personal heat-control device. In this regard, flexible relates to the lack of memory of the material so described or the disinclination of the material to maintain a particular shape other than its original shape. Rather, according to various embodiments described herein, a flexible personal heat-control device band or strip has sufficient adaptability to be incorporated into and/or removably attached to garments and/or accessories, including, but not limited to biking shorts, biking jerseys, exercise suits, sport bras, spandex pants, under garments, shorts, tops, shirts, gloves, shoes, boots, socks, heart monitors, wrist watches, wrist bands, glasses, sunglasses, headphones, medallions, pendants, jewelry (e.g., necklaces, bracelets, anklets), uniforms, baseball caps, golf caps, visors, head bands, hats, chemical suits, bio suits, space suits, space helmets, bullet-proof vests, fire protective suits, motorcycle leathers, goggles, hard hats, motor racing helmets, motor racing undergarments, motor cycle helmets, bicycle helmets, football helmets, batting helmets (e.g. cricket or baseball batting helmets), softball helmets, construction helmets, welding masks, skiing helmets, riding helmets (e.g. equestrian riding helmets), fencing masks, fencing tunics, and the like, so as to move with, adapt and conform to the portion of the body as it bends, moves, flexes, twists, etc.

The term "garment" broadly refers to any article of clothing, apparel, gear, headwear, footwear and/or safety or protective gear. Without limitation, garment as used herein is intended to encompass biking shorts, biking shoes, biking jerseys, exercise suits, sport bras, spandex pants, under garments, shorts, tops, shirts, gloves, shoes, boots, ski boots, roller skates, ice skates, roller blades, socks, wrist bands, heart monitors, wrist watches, uniforms, baseball caps, golf caps, visors, head bands, hats, glasses, sunglasses, headphones, medallions, pendants, jewelry (e.g., necklaces, bracelets, anklets), chemical suits, bio suits, space suits, space helmets, bullet-proof vests, fire protective suits, motorcycle leathers, goggles, hard hats, construction helmets, welding masks, motor racing helmets, motor cycle helmets, motor racing suits, motor racing under garments, bicycle helmets, football helmets, batting helmets (e.g. cricket or baseball batting helmets), softball helmets, skiing helmets, skiing suits and under garments, riding helmets (e.g. equestrian riding helmets), fencing masks, fencing tunics, shin guards, knee pads, military equipment, including hats and helmets, and the like.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phases do not necessarily refer to the same embodiment.

If the specification states a component or feature "may", "can", "could", or "might" be included or have a characteristic, that particular component or feature is not required to be included or have the characteristic.

The phrase "personal heat-control device" generally refers to a portable device that may produce a heating or cooling effect. An example of a personal heat-control device is a personal cooling device (PCD).

FIG. 1A shows an illustrative cross-sectional view of a personal heat-control device 100 constructed as a flexible strip according to one embodiment of the present invention. In this example, a heat transfer unit 101 (indicated by a dotted box) includes one or more TEC modules 104 employing the Peltier Effect (also-known as Peltier modules, thermoelectric modules (TEMs), thermoelectric coolers (TECs), or Peltier-effect units) an optional spreader 102 that functions as a spreader to enlarge the cooling surface of one or more TEC modules 104, and a heat sink block or strip 103 mounted on the hot face of one or more of the TEC modules 104. Examples of how a TEC module may operate are discussed in more detail below.

Figure 1B:
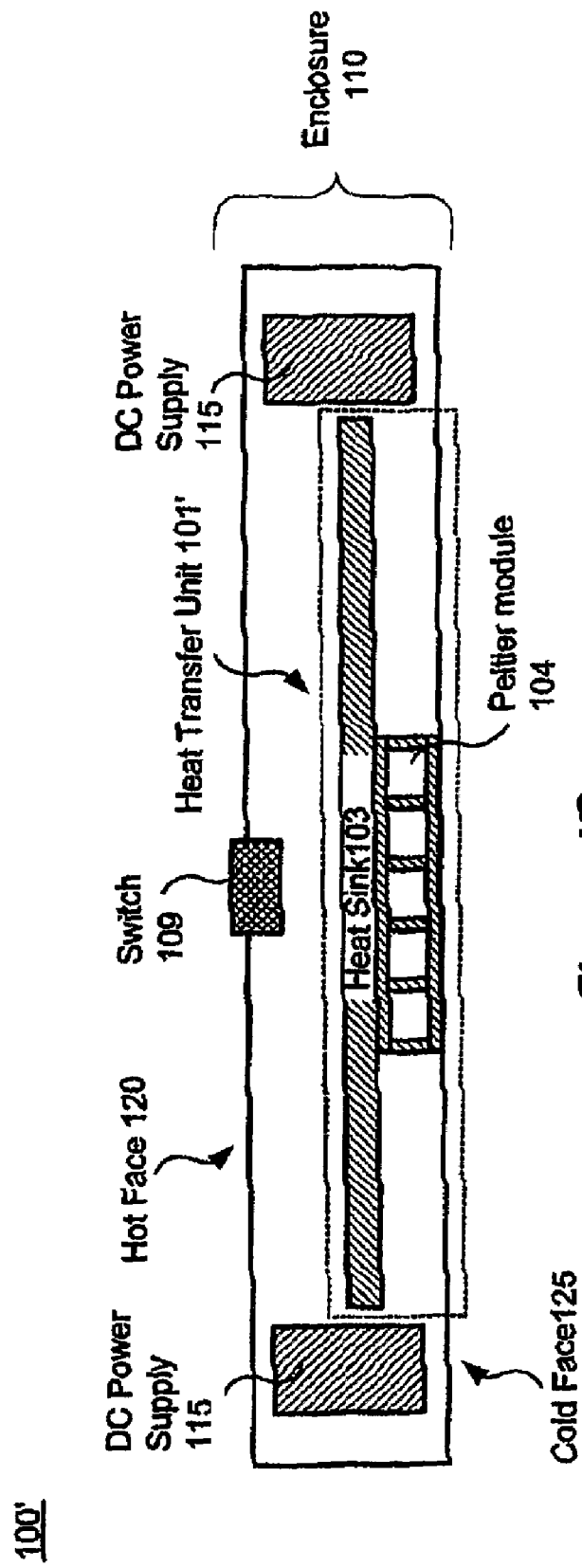
FIG. 1B depicts an illustrative cross-sectional side view of a personal heat-control device constructed as a flexible strip according to an alternative embodiment of the present invention.

According to one embodiment, the spreader 102 is formed of a copper foil or similar conductive alloy, metal, or material, such as aluminum, stainless steel, carbon-fiber, or carbon-carbon materials and/or composites. The dimensions of the spreader 102 may be tailored for the particular application. Empirical data suggests that strips of approximately 0.25 mm thickness, 12 mm width, and 75 mm length is sufficient in terms of flexibility and cooling ability for the baseball cap embodiment, for example, discussed below. According to one embodiment, as depicted in FIG. 1B, the spreader 102 may be excluded from heat transfer unit 101' and the cold faces of the one or more TEC modules 104 may form a cooling surface of an alternative configuration of a personal heat-control device 100'.

The spreader 102, which may be pre-coated by powder coating, in this example, represents the cold face or cooling surface to be exposed on the cold side of the TEC module. The back (inside) surface of the spreader 102 has mounted thereon the cold face of one or more TEC modules 104 fixed with a thermally conductive adhesive, such as double sided tape, epoxy cement or the like.

On the hot face of each TEC module will be mounted an aluminum (or similar conductive alloy, metal, or material, such as magnesium, carbon-fiber, and/or carbon-carbon materials or composites) heat sink block or strip 103, which may be partially or fully exposed on a hot face of the personal heat-control device or ventilated sufficiently via the use of a breathable material enclosure or one or more open channels or troughs in enclosure materials to enable more efficient dissipation of heat. Individual heat sink blocks 103 may be on the order of 1 mm thick, 10 mm wide and 100 mm long. Strip metal heat sinks may be thinner, however, the length should be selected so as to maintain the flexibility of the personal heat-control device for the intended application. As above, a thermally conductive adhesive, such as double sided tape, epoxy cement, a highly thermally conductive heat film adhesive, or the like, may be used to mount the heat sinks onto the TEC modules 104. According to one embodiment, the surface area of the heat sink 103 may be several times the size of the cooling surface with or without the spreader 102, e.g., two to seven times larger depending upon the materials used, to promote rapid heat dissipation. Additionally, the heat sink 103 may be finned to increase its efficiency by increasing the surface area and allowing increased heat dissipation.

Figure 1C:
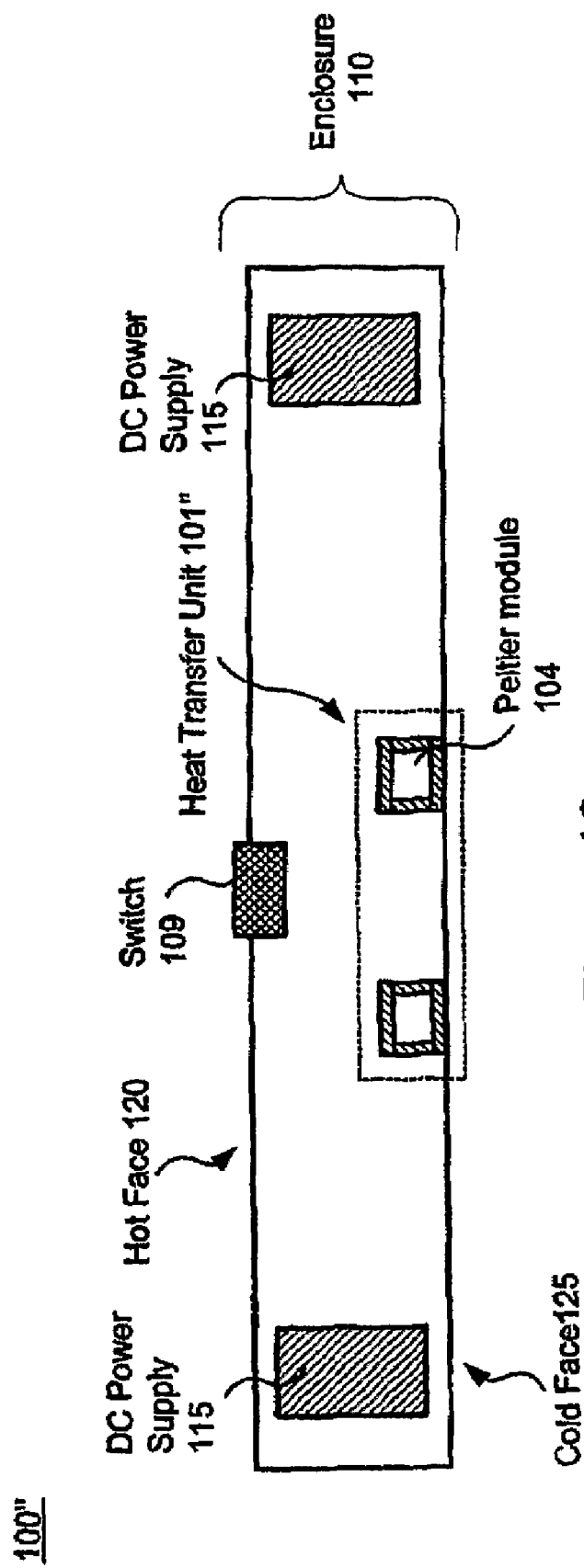
FIG. 1C depicts an illustrative cross-sectional side view of a personal heat-control device constructed as a flexible strip according to another embodiment of the present invention.

According to one embodiment, as depicted in FIG. 1C, the heat sink block 103 may be excluded from a heat transfer unit 101" and the enclosure 110 may function as the heat dissipation mechanism for a personal heat-control device 100". For example, the housing 110 may be the garment itself, and the cooling surface may be integrated separately from the power source and printed circuit board, but within the same garment. In addition, according to some embodiments of the present invention, a circular metal cap or button, such as a bronze cap or button, may be bonded to the cold face of each TEC module for improved safety, comfort, and aesthetic appearance. The bronze in such embodiments may be nickel plated to avoid verdigris (green) marking.

As is well-known, TEC modules are highly efficient heat pumps that directly convert electricity into heating and cooling power. When power is supplied to the TEC modules, the current causes one side of the TEC modules and hence one side of the personal heat-control device (the cool side) to absorb heat. Meanwhile, the other side of the TEC modules (the hot side) release heat (the hot side). That is, the TEC module causes heat to flow from the cool side to the hot side. Reversing the current causes the heat to be moved in the opposite direction thereby reversing the hot side and the cold side. Consequently, according to one embodiment, the heating or cooling effect produced by a particular surface of the personal heat-control device may be selectable by the end user. Based on the disclosure provided herein, one of ordinary skill in the art will recognize the various possible reconfigurations of personal heat control device 100 that would achieve a heating effect, such as, for example, by placing a hot surface of TEC module 104, or a heat sink 103, faced toward the skin or by reversing the direction of current supplied to TEC module 104.

In the embodiments depicted, in FIGS. 1A-C, the basic personal heat-control device elements described above are encapsulated within an optional soft-faced and flexible housing/enclosure 110 constructed of one or more bonded layers of one or more of polyester (polyether), polyethylene, polypropylene, nylon, kevlar, nomex, polyacrylonitrile, cellulose, and polyurethane, or similar foams and/or fibers. Use of flexible, soft-faced materials that are also breathable will facilitate the dispersing of heat generated by the Peltier modules 104 through the housing or enclosure.

According to one embodiment, within the flexible housing 110 are formed chambers of sufficient size and shape to house one or more DC power supplies 115 to power optional electronics, such as a display, e.g., an LCD, to indicate operational and/or battery status, and provide current to the heat transfer unit 101 or 101' or 101". Also, optionally housed are one or more of a timer, a solid-state electronic timing switch 109, an IC chip, and an electro-luminescence (EL) device.

According to one embodiment, personal heat-control device 100, 100' and/or 100" is as convenient to recharge as a mobile phone. The DC power supplies 115 may be Lithium Ion (Li-ion) rechargeable batteries with solid state electrolyte or lithium thin cell primary batteries electrically connected, e.g. by wires or conductive strips, to energize the heat transfer unit 101, 101' or 101" on activation of the solid state electronic timing switch 109 mounted on the outside of the flexible enclosure. According to one embodiment of the present invention, the batteries used to power the circuitry in the personal heat-control device may be Nickel Cadmium (Ni—Cd), Nickel Metal Hydride (Ni-MH) or other type of rechargeable batteries. They can also be disposable batteries. The batteries themselves can be constructed in flexible form, such as those developed by Power Paper Ltd., based in Tel Aviv, Israel. For example, a flexible battery may be printed directly onto paper, plastic or other flexible material. According to yet other embodiments of the present invention, a high-capacity lithium polymer battery may be used.

According to another embodiment, the DC power supplies 115 comprise fuel cells, such as those utilizing methanol cartridges, for example, or solar cells. The DC power supplies 115 may be embedded in a sealed flexible enclosure with the rest of the personal heat-control device circuitry, enclosed in an openable enclosure (particularly suited for disposable batteries or fuel cell cartridges), or external to the personal heat-control device enclosure. Recharging batteries within the flexible personal heat-control device can be achieved via either a 2- or 3-pin flat connector or alternatively a circular connector, for example, any of which can be recessed into the flexible housing 110, on any face of the unit 100, 100' or 100".

On the cold face 125 of the personal heat-control device 100, the soft-faced, flexible housing 110 is cut or otherwise molded or formed to expose, preferably in a flush manner, the spreader 102. On the hot face 120 of the personal heat-control device 100, the soft housing 110 can optionally be cut or otherwise molded or formed to expose the heat sink(s) 103. The outer surface of the hot side 120 may have a Velcro attachment material or similar material, mounted and adhered to it. This material may cover the entire surface of the soft and flexible housing 110 on the hot side 120 of the personal heat-control device 100 with the exception of the heat sinks 103, which may be exposed to assist the dissipation of heat.

It has been found that a pleasant cooling effect is achieved when the unit is activated and the cooling surface or spreader 102 is applied to a portion of the body where blood vessels are close to the surface of the skin for between about 1 to 10 seconds. The timing switch circuitry 109, may prevent or otherwise limit successive reactivation of the unit 100 for a short period, to prevent overcooling, to allow battery recovery, and/or to allow heat generated in the unit 100 to disperse through the hot face 120 of the housing 110. According to one embodiment, the housing 110 may be formed of a thermally conductive material to support more rapid heat dissipation and increase the effective surface area of the heat sink.

Figure 2B:
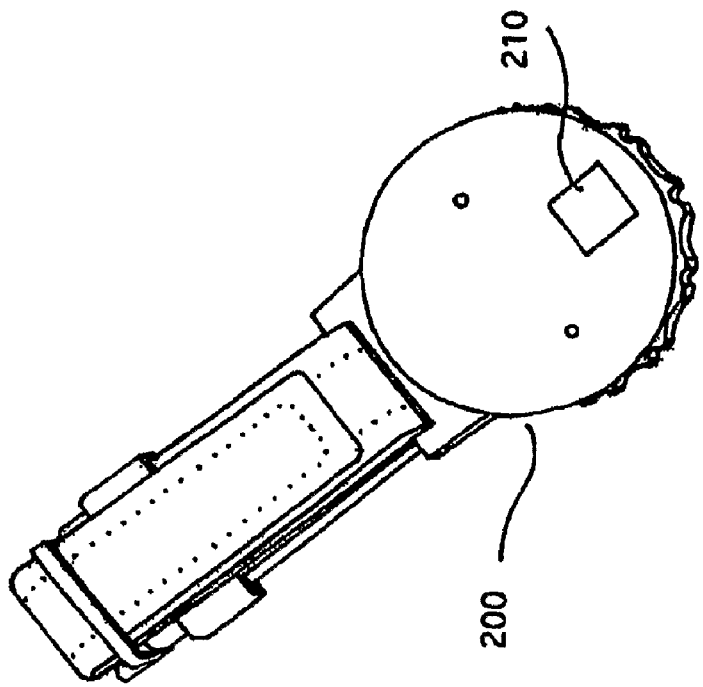
FIGS. 2A and 2B depict front and back views of a personal heat-control device integrated within an ornamental key FOB, pendant or medallion according to one embodiment of the present invention.
Figure 2A:
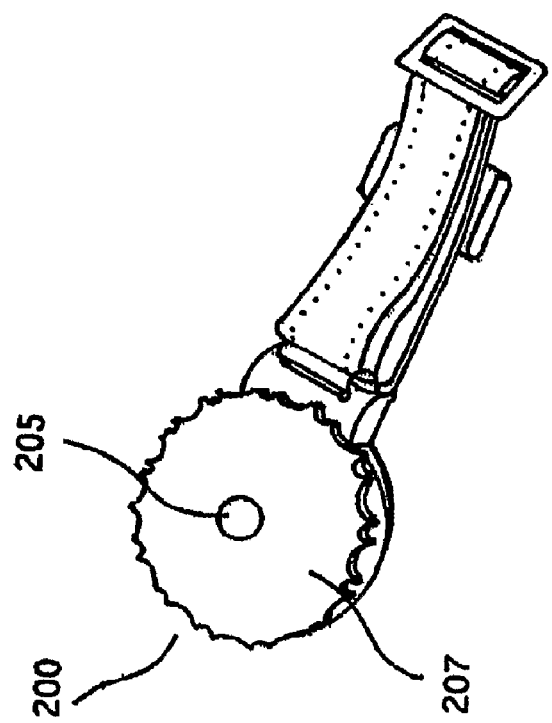

FIGS. 2A and 2B depict front and back views of a personal heat-control device integrated within an ornamental key FOB, pendant or medallion according to one embodiment of the present invention. In the example depicted, a medallion 200 includes an activation switch 205 on the front face. The encasing 207 is formed of aluminum or other metal, alloy, or other heat conductive material and acts as a heat sink. Other heat conductive materials include carbon-carbon materials and composites (e.g., LYASE), and carbon-fiber materials. On the backside, one or more cool spots 210 are provided. While in this example, the cool spot 210 is comprised of the cold faces of one or more TEC modules, in alternative embodiments, an optional spreader may increase the surface area of the cool spot 210.

Figure 4:
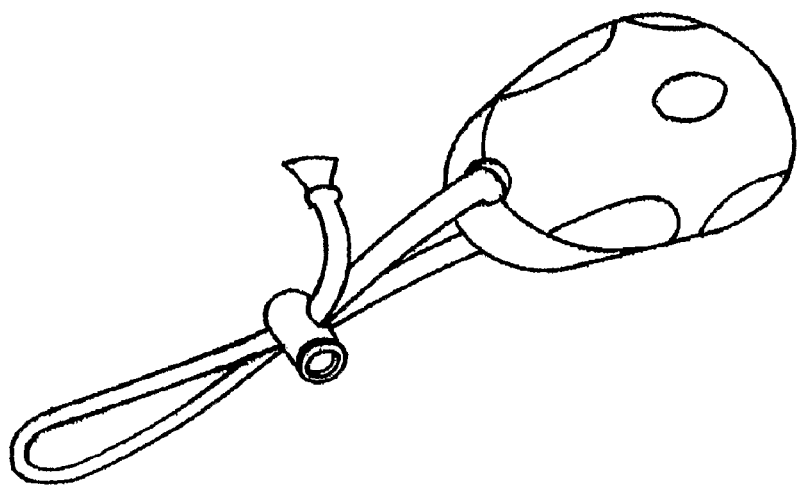
FIG. 4 depicts a personal heat-control device integrated within an ornamental key FOB, such as a model car design, pendant or medallion according to yet another embodiment of the present invention.
Figure 3:
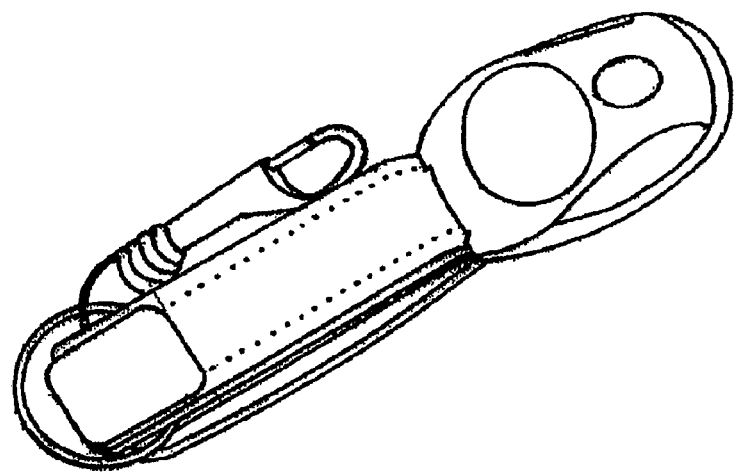
FIG. 3 depicts a personal heat-control device integrated within an ornamental key FOB, such as a mouse design, pendant or medallion according to an alternative embodiment of the present invention.

FIGS. 3 and 4 depict alternative embodiments of a personal heat-control devices integrated within ornamental key FOBs, pendants or medallions.

Figure 5A:
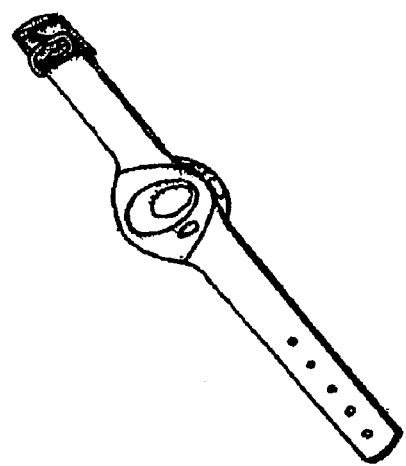
FIGS. 5A-C depict front, back, and side views, respectively, of a wrist watch having an integrated personal heat-control device according to one embodiment of the present invention.
Figure 5C:
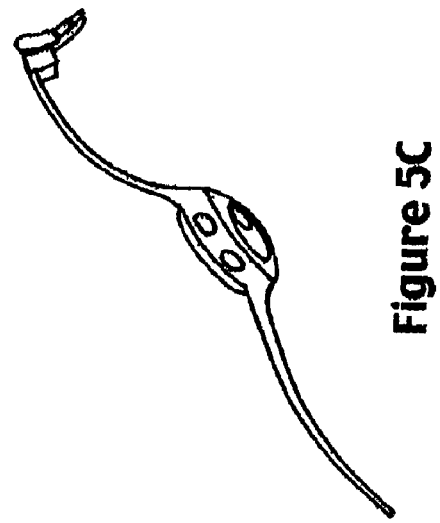
Figure 5B:
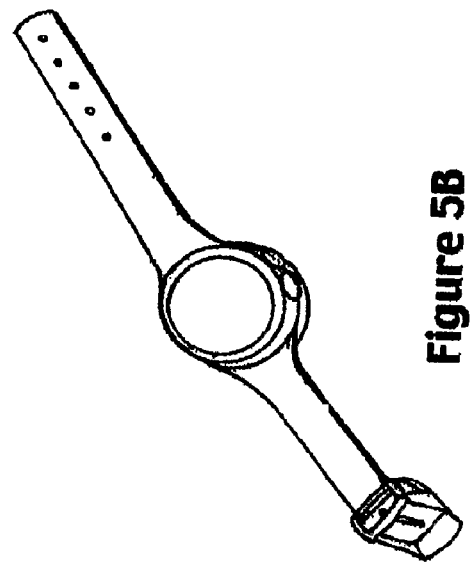

FIGS. 5A-C depict front, back, and side views, respectively, of a wrist watch having an integrated personal heat-control device, such as a PCD, according to one embodiment of the present invention. In an embodiment in which the personal heat-control device is integrated with the watch, the personal heat-control device and watch may share the same DC power source.

Figure 6B:
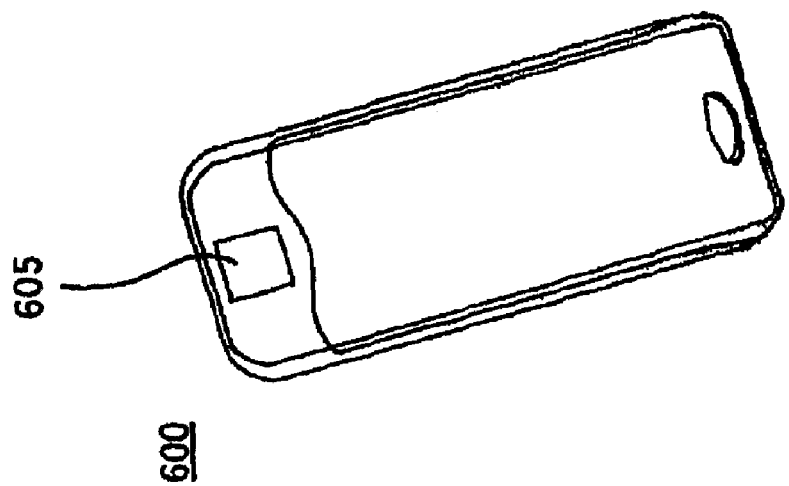
FIGS. 6A and 6B depict front and back views, respectively, of a mobile phone having an integrated personal heat-control device according to one embodiment of the present invention.
Figure 6A:
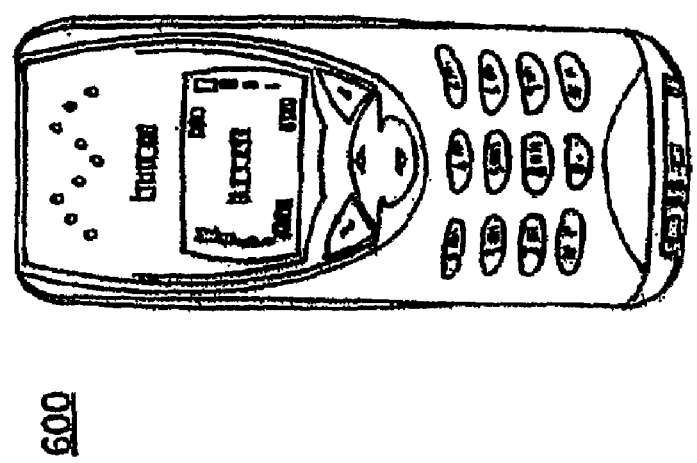

FIGS. 6A and 6B depict front and back views, respectively, of a mobile phone 600 having an integrated personal heat-control device, such as a PCD, according to one embodiment of the present invention. In the example illustrated, one or more cool spots 605 are provided on the backside of the mobile phone 600. Alternatively, cool spots could be positioned on the front side of the mobile phone 600 or they could be present on more than one surface. As above, the surface area of the one or more cool spots 605 may be increased according to alternative embodiments by employing an optional spreader, such as a thin conductive foil. In an embodiment in which the personal heat-control device is integrated with the mobile phone 600, the personal heat-control device and mobile phone 600 may share the same DC power source.

FIGS. 7A and 7B depict a flexible personal heat-control device which may be incorporated within or removably attached to a baseball cap 700 according to one embodiment of the present invention. In the embodiment depicted, a flexible PCD 710 is removably affixed to the baseball cap 700 using a fastener such as a fabric hook-and-loop fastener, such as Velcro strips 705 and 706 or a similar form of attachment. In one embodiment, the device is sufficiently flexible to conform easily to the general shape of the baseball cap 700 and the wearer's forehead.

In the embodiment depicted, the surface of the PCD 710 that will be in contact with the wearer's forehead and/or temples includes one or more cool spots 712 and the opposite side includes the attachment means for attaching to the baseball cap 700 and an exposed heat sink 711.

While in the embodiment depicted, the flexible PCD 710 is illustrated as being removably attachable to the baseball cap 700 and therefore repositionable, one or more flexible PCDs may also be more permanently incorporated within a wearable article in alternative embodiments. For example, in the case of a baseball cap, the flexible PCD may be inserted through a slit in the liner, placed into a preformed pocket in the liner, or even sewn into the liner.

While for sake of brevity an exemplary garment having incorporated therein a personal heat-control device has been described with respect to a baseball cap, according to alternative embodiments of the present invention personal heat-control devices may be incorporated in or attached to various other articles of clothing, apparel, gear, headwear, footwear and/or safety or protective gear using the teachings provided herein.

Figure 8:
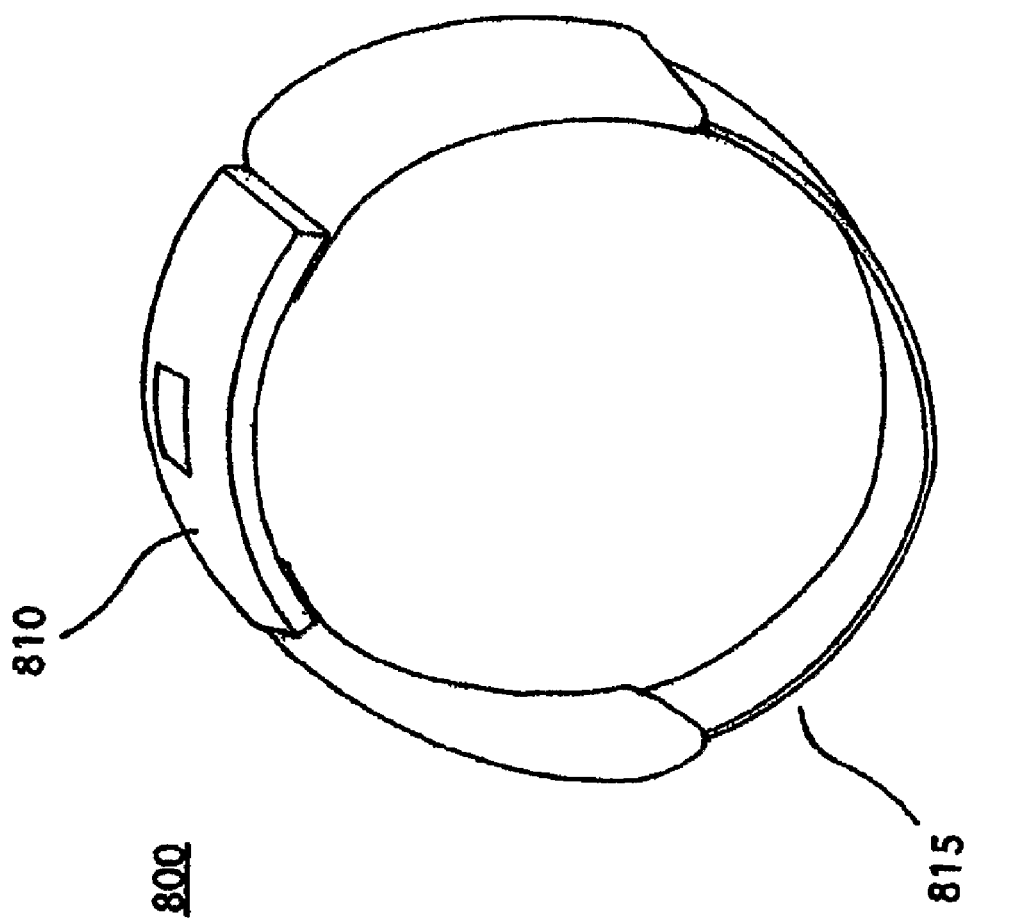
FIG. 8 depicts a head band, wrist band, or the like having a personal heat-control device according to one embodiment of the present invention.

FIG. 8 depicts a band 800 having a personal heat-control device according to one embodiment of the present invention. In this example, the band 800 includes a PCD 810, such as that depicted in FIG. 1 (with or without the flexible housing 110), and a strap 815, such as an elastic loop. The PCD 810 may be fitted into elastic or stretchable material or toweling for comfort and the cold surface may rest directly or indirectly against the wearer's skin. The band 800 may be worn as a head band, wrist band, or the like depending upon the size and configuration of the PCD 800 and the strap 815. According to some embodiments of the present invention, band 800 may be worn around the head with all switching on the outside of band 800.

Figure 9:
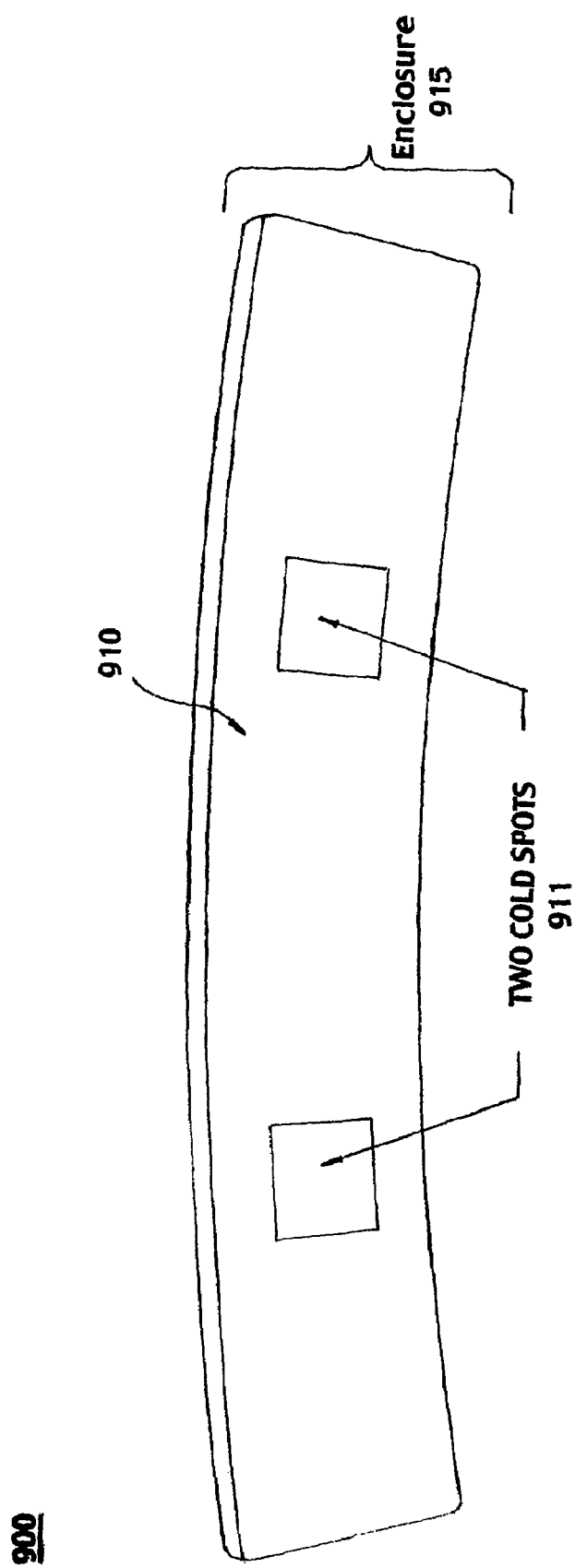
FIG. 9 depicts a cold face of a personal heat-control device constructed as a flexible strip according to an alternative embodiment of the present invention.
Figure 10:
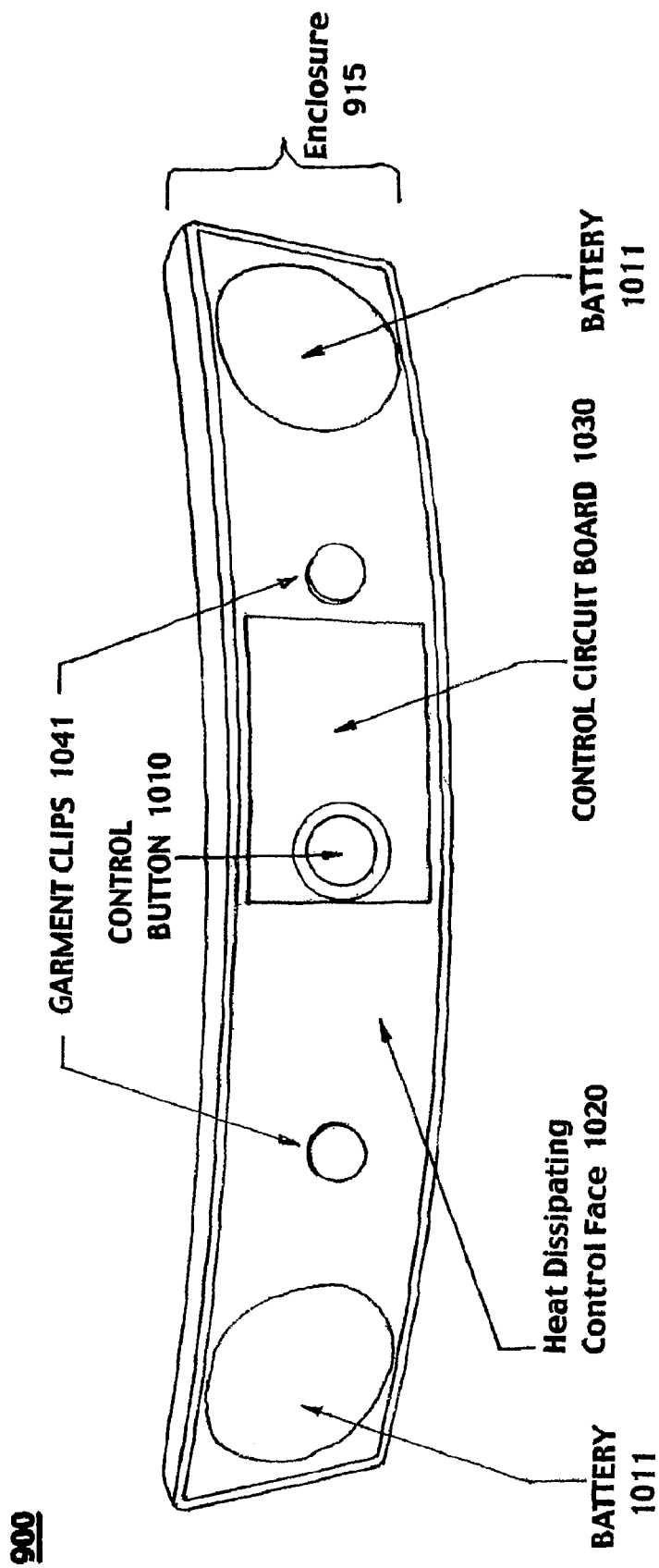
FIG. 10 depicts a heat dissipating control face of the personal heat-control device of FIG. 9.

FIGS. 9 and 10 depict a cold face 910 and a heat-dissipating control face 1020, respectively, of a personal heat-control device 900 constructed as an adaptable strip according to an alternative embodiment of the present invention. In this example, the inside (cold) face 910 exposes two cold spots 911 which may represent the cool faces of two TEC modules mounted to an internal heat transfer unit (not shown), such as a TEC module employing the Peltier Effect (as discussed earlier). According to one embodiment, the dimensions of the cold spots 911 are approximately 1 cm by 1 cm. Depending upon the cooling effect desired, however, more or fewer cold spots may be employed and/or the dimensions may be adjusted accordingly.

As described earlier, TEC modules are highly efficient heat pumps that directly convert electricity into heating and cooling power. When power is supplied to the TEC modules, the current causes one side of the TEC modules and hence one side of the personal heat-control device, i.e., the inside (cold) face 910, to absorb heat. Meanwhile, the other side of the TEC modules (the hot side) releases heat via the heat dissipating control face 1020.

In the embodiment depicted, a control circuit board 1030, one or more batteries 1011, and other personal heat-control device elements are integrated within an enclosure 915. According to one embodiment, the inside (cold) face 910 of the enclosure 915 is constructed of bonded layers of one or more of polyester (polyether), polyethylene, polypropylene, nylon, kevlar, nomex, polyacrylonitrile, cellulose, and polyurethane, or similar foams and/or fibers to provide a soft and flexible face.

According to the embodiment depicted, a heat-dissipating control face 1020 of the personal heat-control device 900 may have formed thereon one or more garment clips 1041 to facilitate attachment of the personal heat-control device 900 to a garment. A control button 1010 may also be included within the heat-dissipating control face 1020 to allow activation/deactivation of the personal heat-control device 900.

According to one embodiment, the heat-dissipating control face 1020 represents or is part of a heat sink that is thermally coupled to the hot side of the TEC modules. The heat-dissipating control face 1020 may comprise aluminum or similar conductive alloy, metal, or material, such as magnesium or copper.

Figure 11:
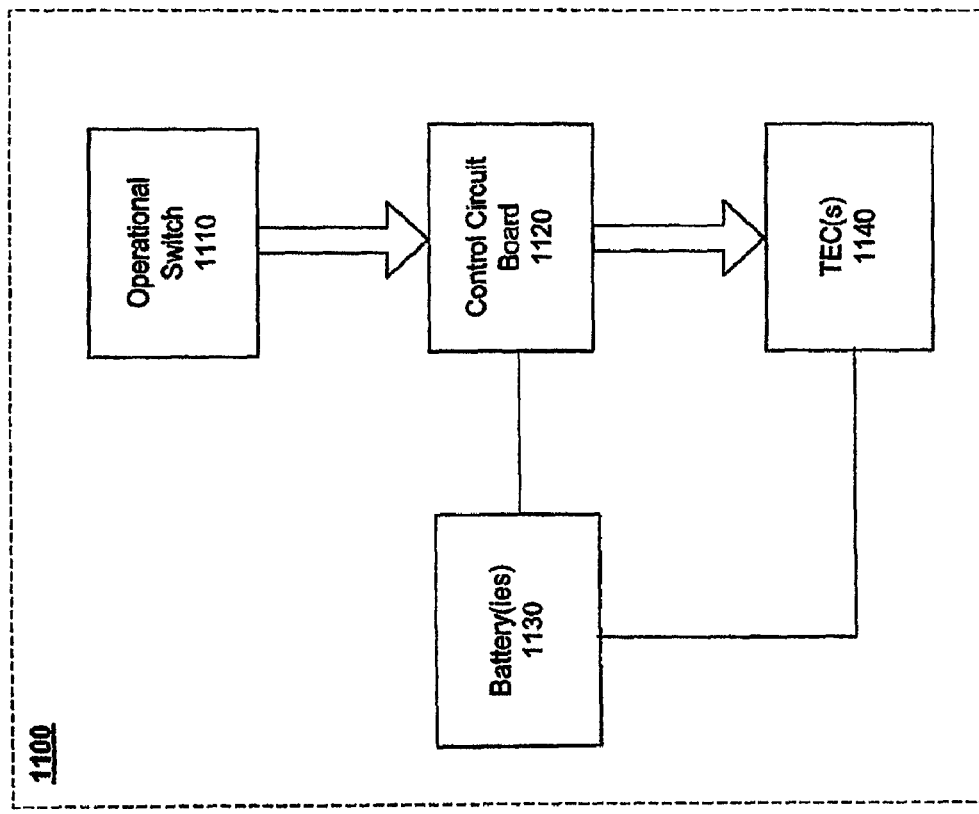
FIG. 11 is a logical illustration of a distributed arrangement of components of a personal heat-control device within a garment according to one embodiment of the present invention.

FIG. 11 is a logical illustration of a distributed arrangement of components of a personal heat-control device within a garment 1100 according to one embodiment of the present invention. In this example, the components that make up the personal heat-control device include an operational switch 1110, a control circuit board (printed or otherwise) 1120, one or more TEC modules 1140, and one or more batteries 1130. The components may be distributed within and/or permanently or temporarily attached to the garment 1100.

Depending upon the particular application or garment, two or more of the components may be co-located or combined. Alternatively, the components may be further broken down into smaller sub-components, for example, individual ICs of the control circuit board 1120 may be separately deployed within the garment 1100, one or more TEC modules may be located remotely from one or more other TEC modules 1140 to provide a more distributed cooling effect. Similarly, batteries 1130 may be distributed within the garment 1100 rather than being clustered together or being placed in proximity to each other.

The operational switch 1110 is communicatively coupled to the control circuit board 1120. The control circuit board 1120 may optionally be communicatively coupled to the TEC modules 1140 to receive temperature information, for example. Such temperature information might be used to increase or decrease the duration of the heat transfer cycle and/or allow other adjustments to be made by control circuitry residing on the control circuit board 1120 to contribute to end-user comfort and/or battery preservation. The batteries 1130 provide DC power to control circuitry and/or timer circuitry resident on the control circuit board 1120 and the TEC modules 1140. According to some embodiments of the present invention, battery 1130 is a lithium-polymer battery. In some cases, a lithium-polymer battery may provide in excess of ten hours of pulsed cooling.

The control circuit board 1120 may include voltage sensing to allow the TEC modules 1140 to be shut down if the voltage being provided to the control circuit board 1120 drops below a predetermined threshold, for example below 1 volt, that would be too low to allow the correct operation of certain circuitry residing on the control circuit board 1120. Such a voltage sensing and shut off mechanism may reduce the risk of the TEC modules remaining energized during a period of time when the control circuitry is inoperable.

The operational switch 1110 may represent a solid-state electronic timing switch operable by an end-user to activate and deactivate heat transfer cycles modulated by optional electronics, such a timer and/or other monitoring or control circuitry. According to one embodiment, the optional electronics provide timed cycling (pulsing) of the TEC modules 1140 to extend operational time per battery charge, to avoid overcooling, to increase the comfort of the user, and/or accommodate battery recovery. According to some embodiments of the present invention, control circuit board 1120 may be a programmable logic device. Control circuit board 1120 may be programmed to pulse or cycle TEC modules 1140 in certain patterns. Such patterns may be predetermined patterns, such as five to ten percent on, then ninety-five to ninety percent off. Such patterns may alternatively include sequencing two or more TEC modules on and off at different times, different durations, and/or different locations to achieve an overall "on" time of approximately five to ten percent. Such patterns may alternatively be based on real-time temperature measurements. Such patterns may be programmed via an external computing source, such as a laptop computer. According to some embodiments of the present invention, control circuit board 1120 may include a radio receiver or transceiver and be programmed and/or reprogrammed via radio signals. For example, the radio control may either be a discrete system or exist via an interface with a voice communication system. According to yet other embodiments, pulsing or cycling patterns of TEC modules 1140 may be in patterns based on intended use; for example, the "on" pulses of TEC modules 1140 may be programmed to last slightly longer to provide greater cooling during an uphill climb of a bicycle race, or to turn off during a fast downhill descent. Empirical testing has determined that, dependent upon their size and configuration, two to eight TEC modules, paired for pulsing in groups of two or three, provide optimal cooling of cephalic blood flow to the temples for ameliorating heat stroke in wearers, such as athletes, military personnel, construction workers, and firefighters. In these ways, pulsing of PCDs on a wearer's forehead may reduce negative cognitive effects associated with overheating.

According to one embodiment, the transmission of one or more of control signaling and/or status information among various of the distributed components is via wireless means. In alternative embodiments, the transmission of one or more of power, control signaling and/or status information among various of the distributed components is via one or more fine conductive wires formed as part of the material of a garment. For example, a plurality of super-fine conductive wires (individually or as twisted pairs of such threads) can be used for sewing seams of the garment or woven into the fabric (natural or artificial) of the garment. In this manner, the fabric could form transmission/communication paths among distributed components 1110, 1120, 1130, 1140 of the personal heat-control device.

Figure 12:
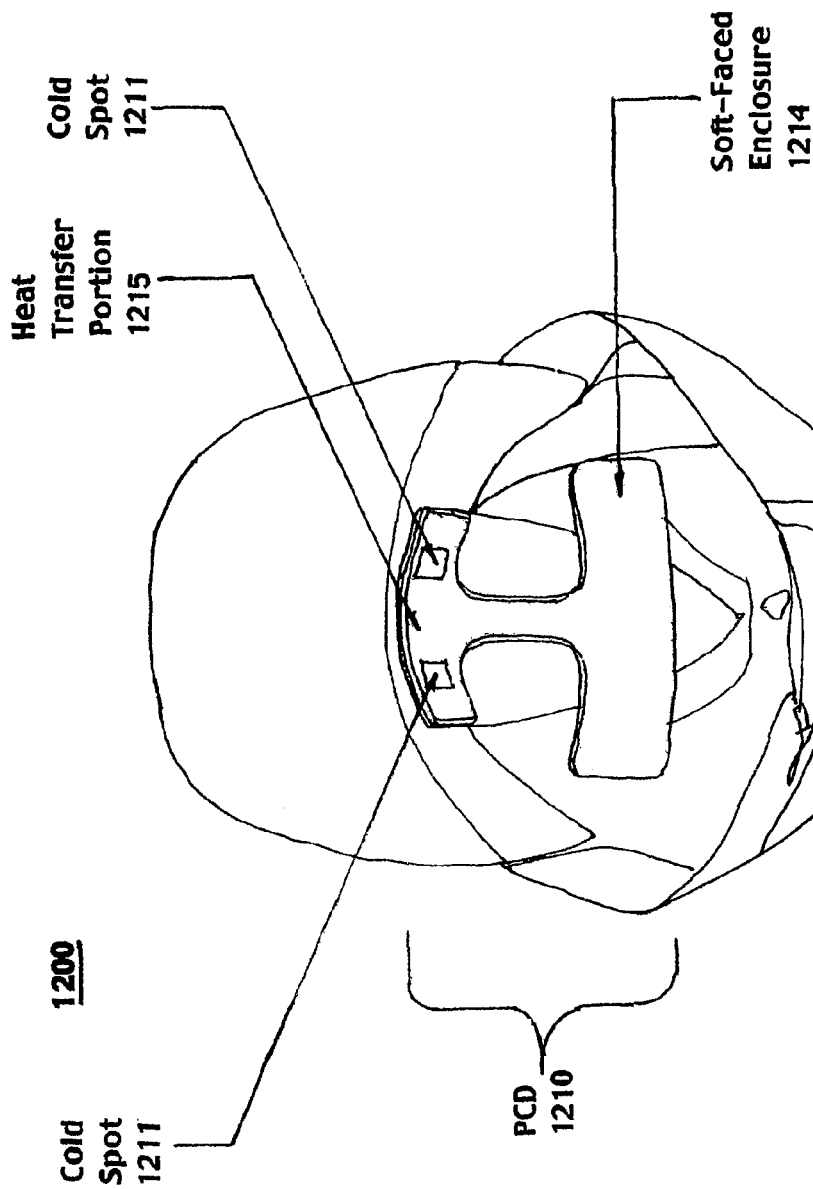
FIG. 12 depicts a flexible personal heat-control device which may be incorporated within or removably attached to a baseball cap according to an alternative embodiment of the present invention.

FIG. 12 depicts a soft-faced and flexible personal heat-control device 1210, such as a personal cooling device (PCD), incorporated within or removably attached to a baseball cap 1200 according to an alternative embodiment of the present invention. In this example, two cold spots 1211 are located in a heat transfer portion 1215 of the PCD 1210 that is positioned along the brim of the baseball cap so as to contact the forehead and/or temples of the wearer. The control and/or timing circuitry, one or more batteries, and switch (not shown) are coupled to the heat transfer portion 1215 but are located apart from the heat transfer portion 1215.

According to one embodiment, a soft-faced, H-shaped enclosure 1214 encapsulates all of the PCD components 1211 and 1215. In other embodiments, some of the PCD components may be located within the soft-faced flexible enclosure 1214 and others may be distributed and incorporated into other portions of the cap 1200.

Figure 13:
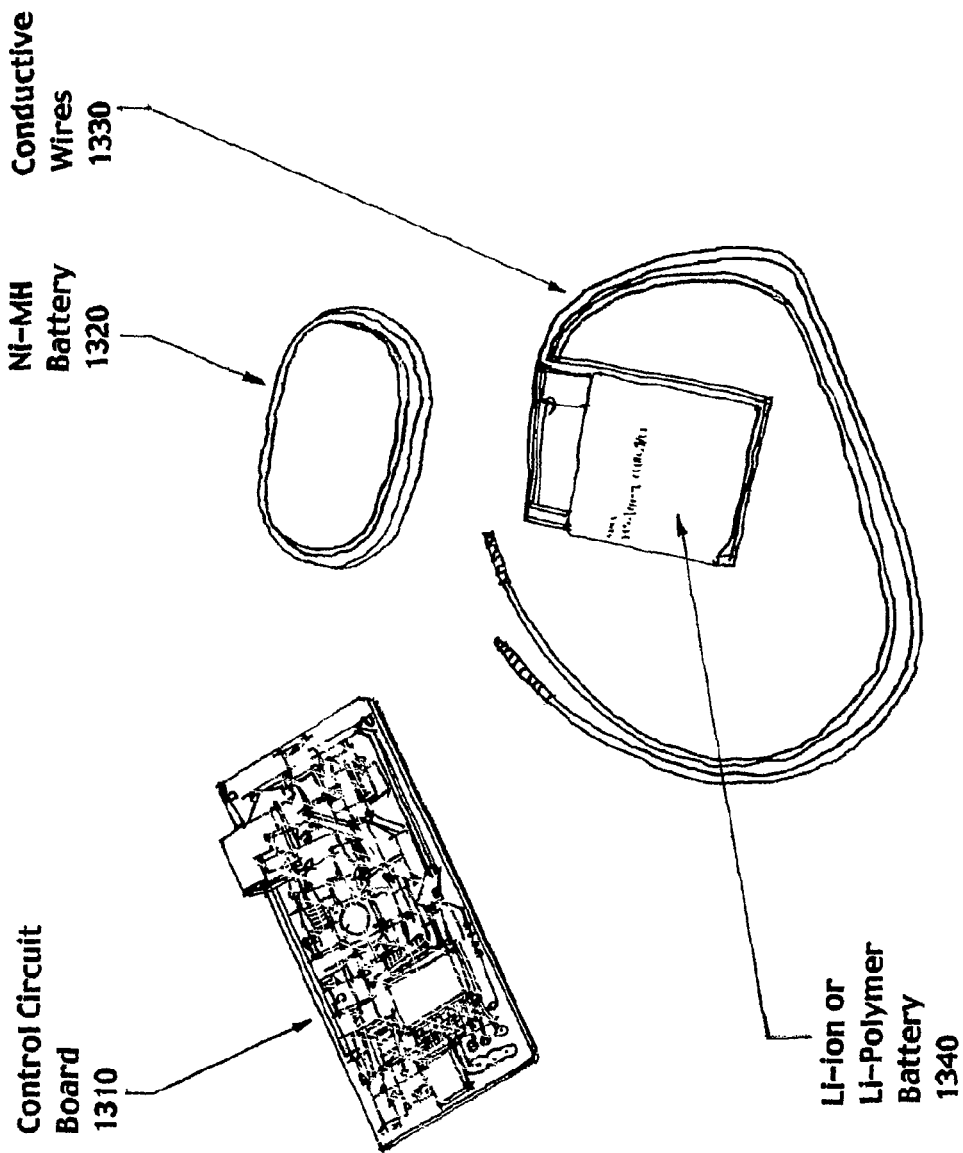
FIG. 13 depicts some representative components of a personal heat-control device according to one embodiment of the present invention.

FIG. 13 depicts representative components of a personal heat-control device according to one embodiment of the present invention, including a control circuit board 1310 having mounted thereon one or more ICs, a nickel metal hydride battery 1320 or a lithium polymer battery 1340, and one or more conductive wires 1330 to provide DC power to the components and/or provide for signaling among the components.

Figure 14A:
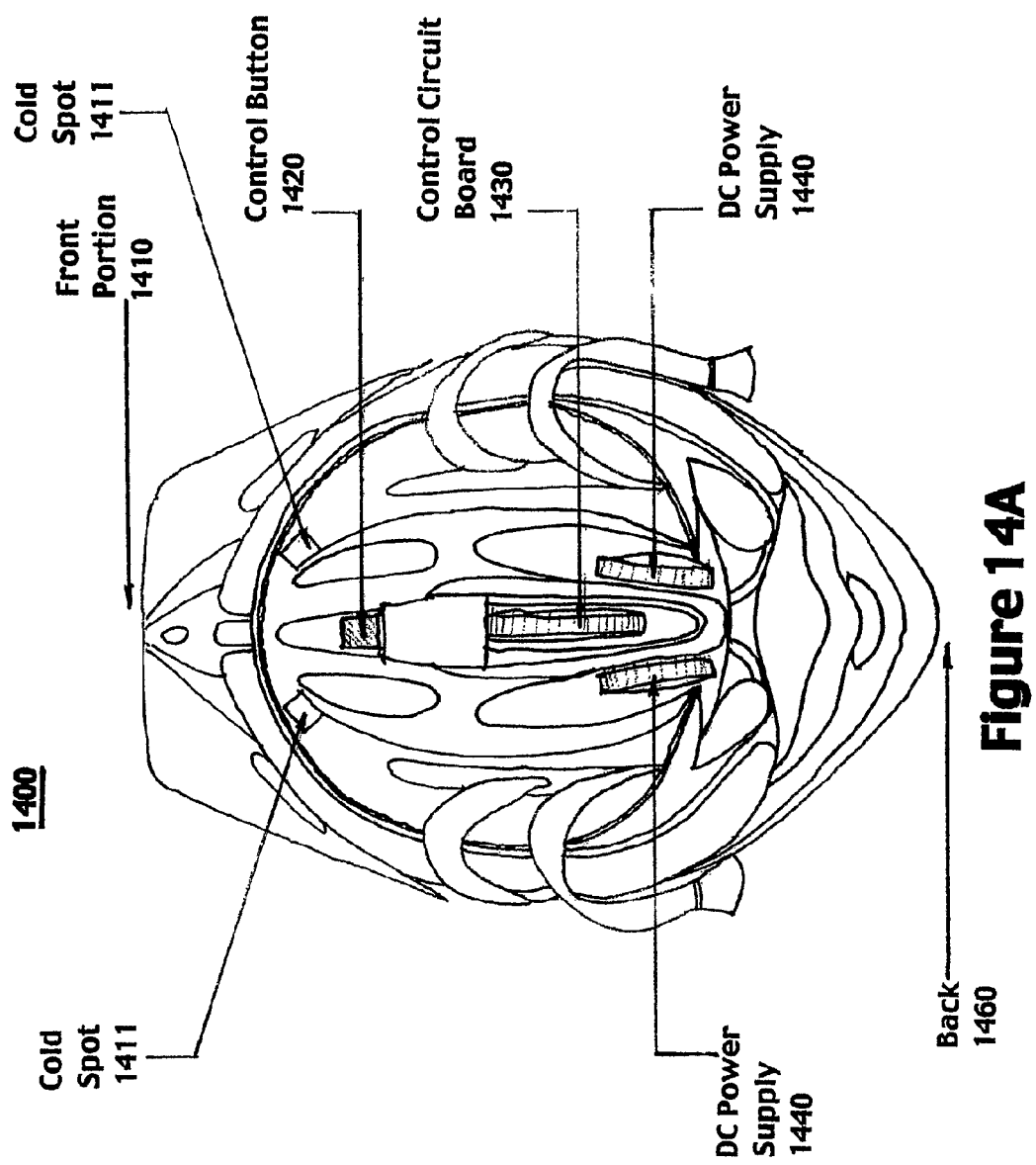

FIGS. 14A-B depict the inside and outside, respectively, of a cycling helmet 1400 having incorporated therein a distributed personal cooling device (PCD) according to one embodiment of the present invention. In this example, the various PCD components are distributed and incorporated into and/or affixed to the frame of the cycling helmet. Two cool spots 1411 are located proximate to a front portion 1410 of the helmet and mounted within the internal molding of the cycling helmet. The control button 1420 is located separate and apart from the cool spots 1411. The control button 1420 is affixed to a top portion of the cycling helmet 1400 within one of the vents, for example, and accessible to the wearer from the outside of the cycling helmet 1400. The encapsulated control circuit board 1430 is located proximate to the control button 1420. DC power supply 1440 is located proximate to the control circuit board. In alternative embodiments, the PCD components may be distributed, incorporated, and/or affixed to the frame of the cycling helmet in other arrangements or configurations. For example, the cold spots 1411 may be positioned elsewhere within the helmet 1400, such as against the temples or against the back of the neck. Additionally, the control button 1420 may be mounted in other locations that are convenient, such as to the visor, in the back 1460 of the helmet or on the right or left side of the helmet. PCD components may also be placed within "fit belts" of the cycling helmet, and may be programmed for racing conditions; for example, the PCD components may be programmed to turn on or off based on the cycling course profile.

Figure 15:
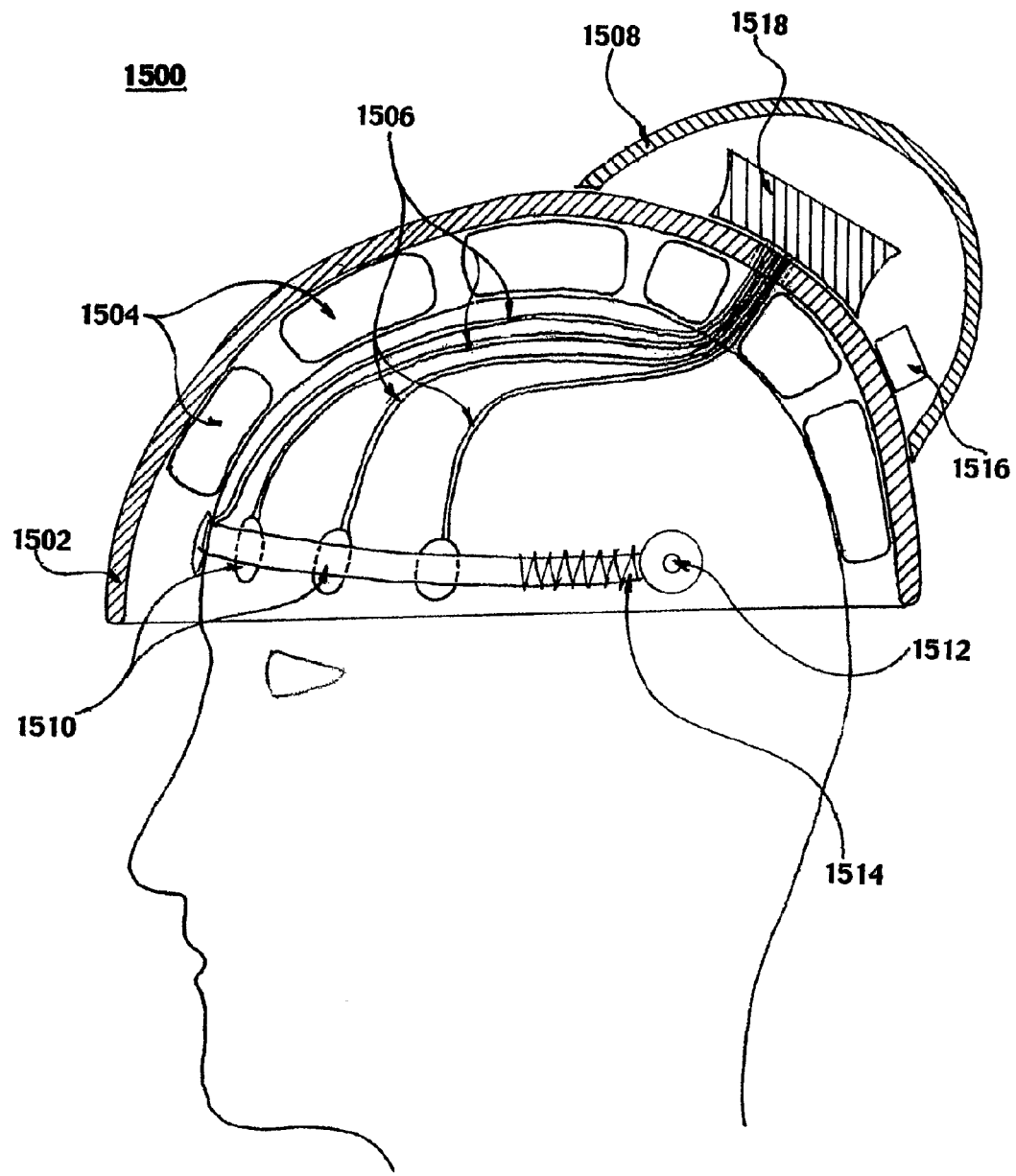
FIG. 15 illustrates a cross-sectional view of an impact-resistant helmet, such as a military or combat helmet, with one or more thermoelectric cooling modules (or cold spots) integrated therein, according to various embodiments of the present invention.

FIG. 15 illustrates a cross-sectional view of an impact-resistant helmet 1500, such as a military or combat helmet, with one or more TEC modules 1510, integrated therein, according to various embodiments of the present invention. An impact-resistant outer shell 1502 protects a wearer's head from impacts such as, for example, bullet or shrapnel impacts, accidental head bumps, and debris impacts. Foam pads 1504 are attached to the inside of impact-resistant outer shell 1502; foam pads 1504 rest on the wearer's head and may serve to dampen the impact force from an object colliding with helmet 1500. For this reason, preferably no part of a personal cooling system should affect the primary purpose of helmet 1500: to increase safety by providing impact and ballistics resistance. Therefore, preferably no part of a personal cooling system should extend between a wearer's head and foam pads 1504, or between foam pads 1504 and outer shell 1502. According to some embodiments of the present invention, foam pads 1504 are interspersed on the inside of outer shell 1502 so as to leave gaps between them. According to some embodiments, TEC modules may be adapted for helmets without foam pads such as, for example, helmets with a traditional fabric web stretched across it.

According to some embodiments of the present invention, TEC modules 1510, rest against a wearer's head. TEC modules 1510 may be secured against the wearer's head by a band, such as, for example, an elasticized band 1514. Elasticized band 1514 may extend across the wearer's forehead and/or temples and attach to the inside of outer shell 1502 via a removable connection 1512 such as, for example, snaps, hook-and-loop closures, pins, knots, clips, nuts, bolts, and/or magnets. Various other means may be employed to secure TEC modules 1510 against the wearer's head; for example, a removable adhesive maybe applied between TEC modules 1510 and the wearer's head. Alternatively, TEC modules 1510 may be secured to an inside surface of outer shell 1502 that is not involved in providing impact-resistance. A "cold face foil" or "spreader" may be placed between the wearer's head and the TEC modules 1510 to better distribute cooling across the wearer's head.

TEC modules 1510 are held against the wearer's head with the cooling surface facing toward the wearer's head and the heating surface away from the wearer's head. Heat pipes 1506 may be thermally coupled with the heating surfaces of TEC modules 1510 on one end, and with a heat sink 1518 on the other end. Heat pipes 1506 are highly thermally conductive conduits that allow the transfer of heat from one location to another with minimal heat loss. Heat pipes 1506 may be constructed of, for example, carbon fiber and/or carbon-carbon materials and composites (e.g., LYASE). Heat pipes 1506 may be flexible heat pipes to increase durability, comfort, and/or wearability. The greater the heat loss of heat pipes 1506, the less efficient will be the cooling. To avoid interference with foam pads 1504, heat pipes 1506 may be positioned within a fit belt structure against the forehead and/or temples and may held in place by a spider web-like pattern so as to extend through the gaps between foam pads 1504. According to one embodiment, the spider web-like pattern may be configured to fit over the scalp. For example, one embodiment of a spider web-like pattern, a "fit belt," and/or a "spider web-type housing," is depicted in FIG. 15. In some cases, any or all PCD components of a PCD assembly may be retro-fittable to existing helmets 1500 and helmet designs. According to some embodiments of the present invention, heat pipes 1506, TEC modules 1510, and elasticized band 1514 comprise a removable cooling unit that may be disconnected from helmet 1500 for cleaning and/or repair. According to alternative embodiments of the present invention, a very highly thermally conductive thermoelectric film may be used in addition to, or instead of, heat pipes 1506, for transferring heat from TEC modules 1510 to heat sink 1518.

According to some embodiments of the present invention, heat sink 1518 is housed within a halo 1508, or accoutrement, on top of outer shell 1502 of helmet 1500. Halo 1508 may be a ventilated external container. A direct current power source 1516 may also be situated within halo 1508. Direct current may be supplied to TEC modules 1510, for example, by connecting direct current power source 1516 with TEC modules 1510 via electrical wires. For example, the electrical wire for each TEC module 1510 may follow the same path as heat pipe 1506 for the same TEC module 1510; in some cases, the heat pipe 1506 and power source wiring may be bundled. In this way, helmet 1500 provides a generally self-contained cooling system.

While exemplary usage models for personal cooling and embodiments of personal heat-control devices have been illustrated and described herein, they are not intended to be exhaustive. Alternative embodiments of the present invention are thought to have broad applicability in the fields of leisure, fashion, healthcare, military, firefighting, construction, industry, and sport. For example, one or more portable and flexible personal heat-control devices may be incorporated within and/or removably attached to athletic apparel or gear, clothing, accessories, headwear, safety or protective gear, including, but not limited to biking shorts, biking jerseys, exercise suits, sport bras; spandex pants, shorts, tops, shirts, gloves, shoes, boots, socks, heart monitors, wrist watches, wrist bands, glasses, sunglasses, headphones, medallions, pendants, jewelry (e.g., necklaces, bracelets, anklets), uniforms, baseball caps, golf caps, protective clothing (e.g., surgeon caps, gardening hat, sun hat), police or military caps/hats or headgear, visors, head bands, hats, chemical suits, bio suits, space suits, bullet-proof vests, fire protective suits, motorcycle leathers, goggles, hard hats, motor racing helmets, motor cycle helmets, bicycle helmets, football helmets, batting helmets, skiing helmets, firemans helmets, welding goggles, riding helmets, construction helmets, and the like.

Furthermore, personal heating devices may be incorporated into or attached to ski boots, ski poles, gloves, mittens, snow shoes, snow boots, ski jackets, snow boards, skis, toboggans, sleds, sleighs, or other winter sporting/leisure equipment, accessories, or garments.

In addition to sales of personal heat-control devices built into garments, it is contemplated that personal heat-control devices will be sold as kits for insertion into or attachment to various types of garments.

According to other embodiments of the present invention, a PCD may be part of a stand-alone dedicated portable cooling device or integrated into or temporarily affixed or attached to other conventional consumer products or devices, including, but not limited to water bottles (as coolers, for example), camel back liners or bladders, cameras, key chains, pulse monitors, electric shavers, hand held razor blade holders for use with either metal or ceramic blades, key FOBs, pendants, mobile phones, pagers, personal digital assistants, spectacles, hearing aids, jewelry, etc.

Optionally, the personal heat-control device may include timers or EL devices. Their operation can be modulated by one or more IC chips. For example, the PCD could employ a timing device modulated by an IC chip to periodically activate cooling for a predetermined (e.g., 10, 15, 30 seconds) or user-adjustable amount of time. Additionally, the timing device may control the minimum time between operations in order to allow batteries to recover and/or allow appropriate heat dissipation. According to one embodiment, the TEC modules may operate in accordance with multiple modes of pulsed operation, e.g., a single cold pulse per cycle or multiple pulses per cycle.

EL technology (electro-luminescence) can be incorporated into a personal heat-control device according to one embodiment of the present invention. For example, a strobe light of white, red or blue color can be used to accompany the operation of a PCD to indicate, among other things, the "on" state of the personal heat-control device and cooling or heating operation of the personal heat-control device. Pulsating strobe lights can be modulated by an IC chip. The voltage needed for the strobe lights can be produced by, for example, high frequency power converters.

Various other embodiments of the present invention are described below.

It has long been accepted that overheating in humans leads to their distress, accompanied by both physical (e.g. head edema, dehydration, decreased muscle efficiency, heat exhaustion, heat stroke) and mental impairments (e.g. decreased attention, vigilance and reaction time) and even leading to death. This problem is most seriously identified by excessive temperature increases to the cephalic (head) regions. In recent years this distress has been most identifiable and measurable in sporting performances. It has been ascertained that heat stroke is the second largest cause of death in athletes. Heat stroke is a true medical emergency brought on by markedly elevated body temperature (>105° F.) that can result from heavy exceptional activity in conjunction with high temperatures and humidity and which can be exacerbated by the wearing of head gear. In addition, mental impairment has been shown to set in at a body temperature of just 100.4° F. with complete disruption of neural function by 107.6-115.7° F. As such this is a real concern for military personnel. Soldiers typically have to deal with all of these elements including wearing a protective helmet, whose structure is not ideal (with its heavy Kevlar construction, little ventilation and thermal insulating qualities), in the battlefield. Thus, soldiers in active combat in hot climates will as a direct result of wearing a combat helmet, suffer (to one degree or another) from an inability to fully perform in accordance with their highest standards, because their response times will have been slowed and their decision making skills impaired. A leap in modern military apparel may be achieved with the development of the Personal Cooling Device (PCD). Embodiments of a PCD system may provide the military services with a pioneering tool that when integrated into the modern combat helmet will enable control of the user's cephalic blood core temperature. This capability could prove to be invaluable in the battlefield, by providing the means to eliminate the aforementioned physical and cognitive impairments associated with heat stress, suffered by helmet wearers.

PCD technology combines features of thermoelectric cooling, heat ducting/dissipation techniques and innovative operational patterns, and may be used in an advanced cooling system. Embodiments of the present invention are a safety device, designed to save lives and improve the physical and mental performance of the wearer as well as enhance overall comfort. Specifically, an active cooling technology with no fans, sprays or crystals may be achieved. Reliable cooling may be achieved with no moving parts. The Personal Cooling Device (PCD) may be installed either within new combat helmets or be retrofitted within existing units. Unlike previous attempts to install cooling within headwear, the PCD may provide pulsed thermoelectric cooling to the forehead and temples for in excess of 10 hours of continuous operation between battery re-charging, thus meeting the requirements for "day long" wearing.

The integration of high capacity lithium polymer re-chargeable battery technology with multiple TEC modules, together with an efficient heat pipe/heat sink arrangement, may enable a suitable heat pump assembly, which may add less than 3% to the weight of a Kevlar combat helmet. According to some embodiments of the present invention, such an assembly should not impinge upon the impact resistant qualities of the helmet and as such should not come into contact with the helmet shell, under any reasonable impact conditions, even indirectly via the removable impact pads located within the helmet.

Some possible features of a PCD system according to various embodiments of the present invention may include:

Pulsed operation—pulsing of the PCD system may be more in harmony with the natural pulsing of blood throughout the cephalic regions and as such may enable more efficient cooling. It may be seen to resemble 'the rolling of a cold can of soda across the forehead and temples' a sensation often welcomed in hot and humid conditions. In addition, embodiments of a PCD's pulsed cooling action may provide advantages over other systems: 1) the 'on/off' comfort factor that is more conducive to the user than the unpleasant stinging sensation usually experienced with any constant and widespread cephalic cooling; 2) the 'off' phase allows sufficient time for the heat to be dissipated from the assembly; and 3) the 'off' phase also allows the battery to recover its ability to efficiently discharge its full capacity, thereby extending the period of operation between re-charging.

Long-life—embodiments of the present invention capitalize on the use of modern lithium polymer high capacity re-chargeable batteries, which depending upon the set pulse operation pattern can provide more than ten hours of continuous pulsed use, meeting the requirements for 'day-long' wearing without recharge.

Elimination of mechanisms—eases integration, enables high reliability standards and reduces weight.

Rugged construction—can be made to be very rugged and robust in construction to meet the demands of the field.

Configurable—easily installed within helmets, new or retrofitted within existing units. The lithium polymer batteries may be molded to suit the curves of a helmet.

Lightweight—may add less than 3% to the weight of a helmet.

Figure 16:
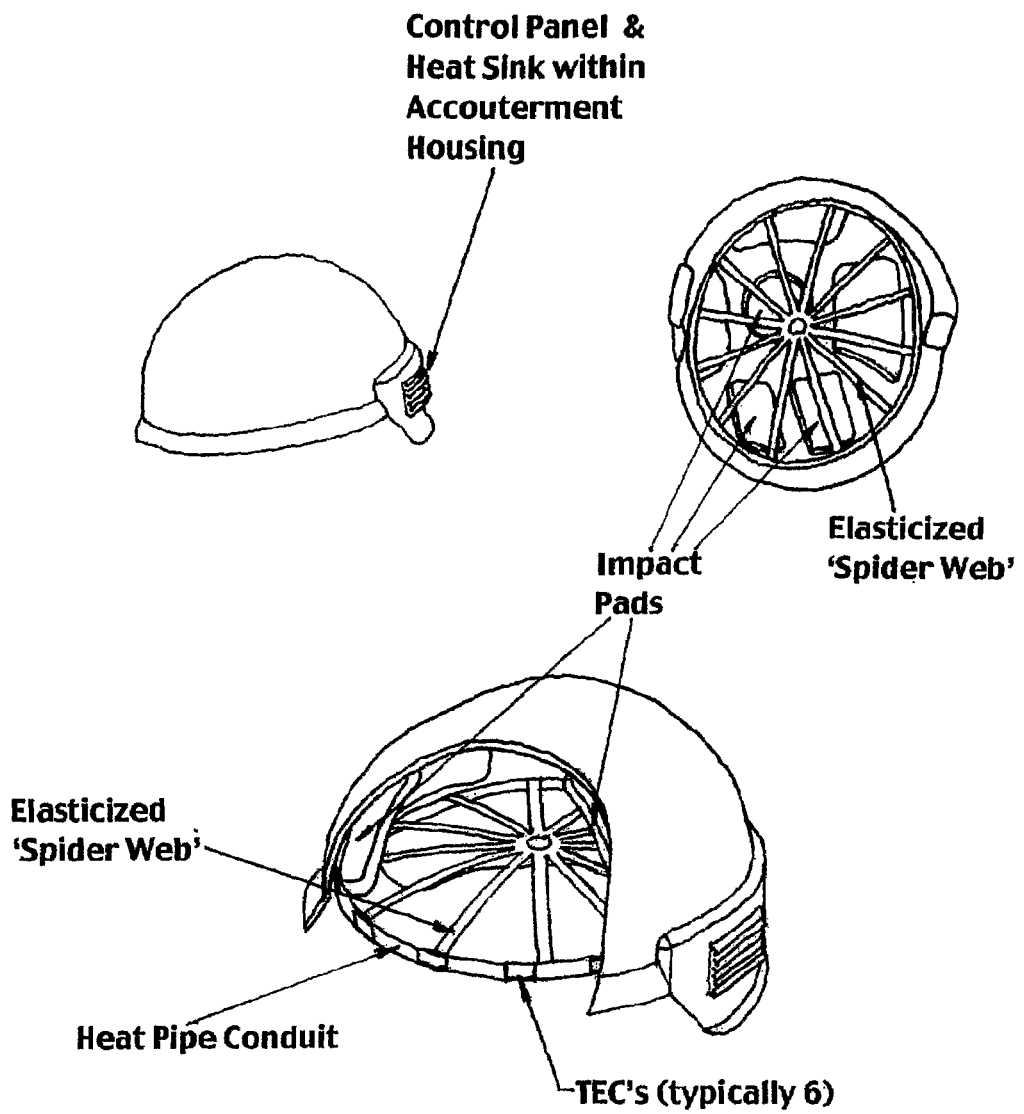
FIG. 16 illustrates perspective isometric views of an impact-resistant helmet, such as a military or combat helmet, with one or more thermoelectric cooling modules (or cold spots) integrated therein, according to various embodiments of the present invention.

A conceptual drawing of one possible embodiment of the PCD system housed in a military combat helmet is shown in FIG. 16. Embodiments of a PCD assembly may comprise four components: 1) TEC modules, 2) heat sinks & heat pipes, 3) control panel (with switching) and 4) DC power. An embodiment as illustrated for integrating the PCD system into a combat helmet involves using a 'spider web' lining construction, such as the use of an elasticized webbing design that provides the means to hold the TEC modules, foil 'spreaders', heat pipes and wiring in place. In addition, due to the 'spider web' being tensioned, this arrangement may also ensure that the pulsed cold faces of the TEC modules obtain full contact with the forehead and temples of the user, possibly via a foil linking the TEC modules to spread the cooling surface. The suspended nature of the 'spider web' assembly may also prevent the PCD system from contacting the helmet shell or the foam impact pads so as not to impinge upon the helmet's impact resistant qualities. The internal components of the PCD system may be attached to the helmet with Velcro. It can also be seen from FIG. 16 that the proposed PCD system design concept retains the impact pad arrangement (normally six) within the helmet to provide safety cushioning and comfort, and incorporates six TEC modules and two heat pipe conduits that carry the expelled heat to two heat sinks which are mounted externally on either side of the helmet's shell but within an accouterment housing that is louvered for ventilation and protected from solar radiation.

Each application of TEC modules to garments may have different requirements. For example, the dissipation of heat from the open gauze of a heavy fencing mask involved issues of constant removal of the mask, together with the fact that the mask was often thrown off onto the ground (following referee's decisions). Therefore, TEC modules had to be accurately located and made robust. TEC module installation within an open lattice road cycling helmet involved aerodynamic issues, weight and impact issues, and TEC module installation into a cricket helmet had enclosure issues not unlike a combat helmet.

According to some embodiments of the present invention, efficient heat pipes may be flexible and fabricated as a laminate of polypropylene, metal and adhesive layers or may involve a carbon fiber braiding, encased in an epoxy polymer matrix. Improved dissipation of heat may require thermally conductive adhesives between each component through the 'chain' of conductivity. One example of a heat pipe which may be used in accordance with various embodiments of the present invention is manufactured by RMACore International, Inc.

Figure 17:
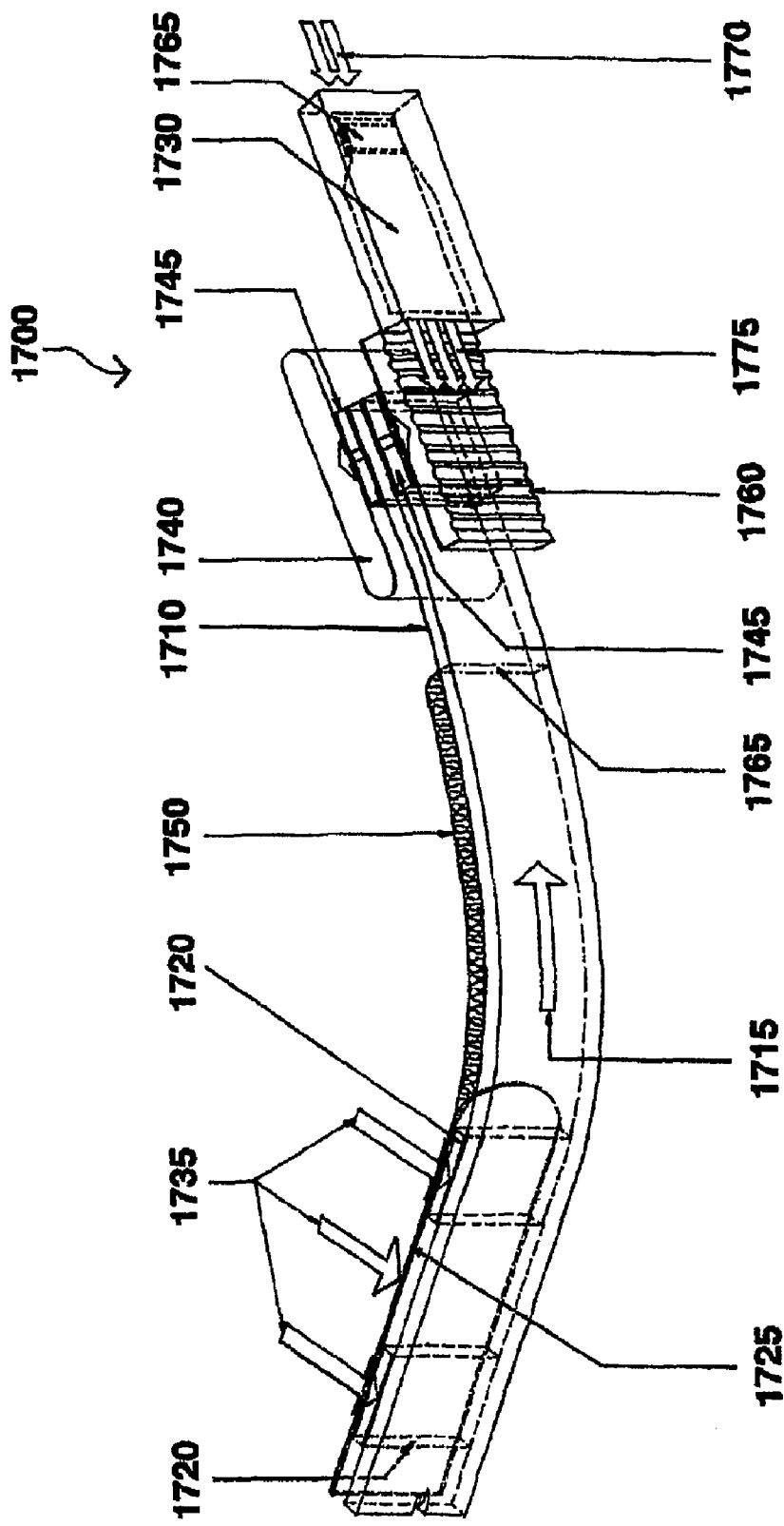
FIG. 17 illustrates a personal heat-control device comprising a heat pipe which may be used in accordance with various embodiments of the present invention.

FIG. 17 illustrates a personal heat-control device comprising a heat pipe which may be used in accordance with various embodiments of the present invention. In the embodiment depicted in FIG. 17, personal heat-control device 1700 may be used to remove heat from a first location to a second location. For example, personal heat-control device 1700 may be used to remove heat from inside an insulated helmet, or other garment, to an external location of ambient air. According to various embodiments personal heat-control device 1700 may include one or more of a heat pipe 1710, TECs 1720, 1745, a piezoelectric resonant fan 1730, phase change material 1740, padding 1750, and/or a heat sink 1760.

A heat pipe is a device that is capable of quickly transferring heat from one point to another. In particular, a heat pipe is capable of transporting heat with a very small difference in temperature between hot and cold interfaces. According to one embodiment, one end of a heat pipe may be thermally connected to the hot faces of one or more internal thermoelectric coolers (TECs) 1720, or thermoelectric film, while the other end of the heat pipe may be thermally coupled to one or more cold faces of one or more external TECs 1745, or thermoelectric film, which may be attached to heat sink devices 1760 and/or phase change materials 1740. Heat pipes are often referred to as 'superconductors' as they may possess an extraordinary heat transfer capacity and rate, with almost no heat loss.

As known to those skilled in the art, a heat pipe typically consists of sealed tube, a small amount of liquid coolant, and a vapor phase of the coolant, for example. According to one embodiment, the tube may be made of a thermo-conductive metal such as copper, aluminum, and the like. Examples of typical coolants include, but are not limited to, water, ethanol, mercury, and the like. As known to those skilled in the art, the choice of materials and coolant may depend, at least in part, on the temperature conditions in which the heat pipe operates. For example, coolants such as liquid helium may be used for extremely low temperature applications while coolants such as mercury may be used for high temperature conditions. According to one embodiment, heat pipe 1710 may be fabricated as a flexible and flattened laminate of polypropylene, with a sealed aluminum or copper container and adhesive layers, with a total thickness of less than 3 mm.

With the use of 1710 heat pipe, heat is transported 'passively' against gravity by an evaporation-condensation cycle. In some heat pipes, which may be used in accordance with various embodiments of the present invention, heat is transported with the help of porous capillaries that form a wick. The wick also provides the capillary driving force to return the condensate to the evaporator at the end of the cycle. Some heat pipes, which may be used in accordance with embodiments of the present invention, may contain a wick structure capable of soaking up the coolant. In addition, various heat pipes may contain no moving parts and typically require no, or very little, maintenance.

Fundamentally, heat pipes rely on a temperature difference between the ends of the pipe. As such, when one end of the heat pipe is heated, the coolant inside the pipe at that end evaporates and increases the vapor pressure inside the cavity of the heat pipe. The latent heat of evaporation absorbed by the vaporization of the coolant reduces the temperature at the hot end of the pipe.

The vapor pressure over the liquid coolant at the hot end of the heat pipe is higher than the equilibrium vapor pressure over condensing coolant at the cooler end of the pipe, and this pressure difference drives a rapid mass transfer to the condensing end where the excess vapor releases its latent heat, warming the cool end of the pipe. In the embodiment depicted in FIG. 17, arrow 1715 indicates the direction of heat flow from the internal TECs 1720 to external components and ambient air.

The condensed coolant then flows back to the hot end of the pipe, either by force of gravity in the case of vertically oriented heat pipes, or through capillary action in the case of heat pipes containing wicks, or heat pipes that are oriented horizontally relative to gravity. One advantage of using a heat pipe is the great efficiency in transferring heat.

According to some embodiments, the use of heat pipes within 'PCD' technology may be well-suited in applications involving highly insulating headwear. For example, embodiments of the 'PCD' technology using heat pipes may be useful in a Kevlar combat helmet where the heat sinks must be located remotely from the cold faces, in an external location.

In addition to a heat pipe, various embodiments may also include one or more TEC devices. According to one embodiment, a PCD device may include one or more internal thermoelectric cooling modules 1720, known as a TEC. In accordance with various embodiments, TECs 1720, 1745 may be small solid-state devices that can operate as heat pumps utilizing the Peltier Effect. This phenomenon occurs when a DC electrical current is passed through the junction of two different types of conductors, resulting in a temperature differential across the module.

According to one embodiment, semiconductors that are good conductors of electricity but poor conductors of heat may be used to created a good balance for TEC performance. For example, bismuth telluride may be primarily used as the semiconductor material, heavily doped to create either an excess (n-type) or a deficiency (p-type) of electrons.

Very simply, TECs 1720, 1745 may consist of a number of p- and n-type pairs (couples) connected in series and sandwiched between two ceramic plates. When a TEC is connected to a DC power source (not shown), current causes heat to move from one side of the TEC to the other, which naturally causes a hot and cold side on the TEC. According to one embodiment, the cold side faces the skin and the hot side is attached, possibly through a heat pipe, for example, to a heat sink, which dissipates the heat to the environment. In one embodiment, aluminum foil 1725 may be used to connect two or more internal TECs 1720 in order to form a cold face against the user's skin. In another embodiment, a cold face may be created by a fluid filled vinyl bag connecting TECs 1720.

For example, according to one embodiment the PCD may be placed in a helmet in such a fashion that some internal TECs 1720 are positioned to align with the temples and forehead of the user. In this case, heat will flow, as shown by arrows 1735, from the temples and forehead to a spreader/foil 1725 to internal TECs 1720 to heat pipe 1710.

According to one embodiment of the present invention, the thermoelectric technology for the 'PCD' may include thin-film thermoelectric cooling technology. This technology includes solid-state refrigeration devices that may offer a higher cooling density, a smaller form factor and higher reliability than traditional TEC modules. The thermoelectric film improves system performances and lifetimes and reduces the size of the cooling component. By matching the cooling density of the film to the heat source, overall power efficiencies within the 'PCD' can be significantly increased. Various embodiments of the present invention include 'PCD' applications that will generally use either thermoelectric film or two or more internal TECs 1720, powered in pairs and connected on their cold faces by a foil 1725 (or spreader) to form a smooth and comfortable cooling surface against the skin.

Some embodiments may use one or more heat sink devices 1760. For example, according to an embodiment illustrated in FIG. 17, heat sink 1760 is coupled to one or more TECs 1720, 1745 by heat pipe 1710. In one embodiment, heat sink 1760 may be finned or fluted. Heat sink 1760 may be made of any good thermal conductor such as aluminum, copper, and/or the like. According to one embodiment, the use of the heat pipe 1710 allows heat sink 1760 to be located in a variety of places. For example, the heat pipe may pass through a garment, around a garment or a helmet, and/or attached to the edge of a garment or helmet. The point at which a heat pipe may leave the padded interior of a helmet to an exterior portion or accouterment is indicated by element 1765. According to some embodiments, one or more components, such as a heat sink, phase change materials, external TECs, and/or the like may be located outside of the garment or within an accouterment or halo. For example, heat pipe 1710 may be routed through a hole in the garment, come out under a lip, and/or around an edge of a garment in order to dissipate the heat away from the user. Importantly, the use of heat sink 1760 in conjunction with the one or more TECs 1720, 1745 may allow for heat to be moved away from the system.

According to one embodiment, attached to the hot side of external TEC modules 1745 (or thermoelectric film) may be heat sink 1760 and/or phase change material (PCM) 1740. In some embodiments, TECs 1720, 1745 are adhered to heat sinks, spreaders, phase change materials, heat pipes, and/or the like via flat surfaces with a thermal compound. Examples of such thermal compounds known to those skilled in the art include, but are not limited to, thermally conductive grease containing colloidal silver, silicone based grease, ceramic based grease, or other metal based greases. The precise design of heat sink 1760 may depend upon the particular 'PCD' application, but should enable air to quickly pass across its surface, which may be 'finned' or fluted for efficient aerodynamics, to have sufficient mass, and to create a larger surface area for heat dissipation to the environment.

In one embodiment, phase change materials (PCMs) may be used either on their own or in combination with heat sinks. A PCM is a substance with a high heat of fusion which, melting and solidifying at certain temperatures, is capable of storing or releasing large amounts of energy.

PCMs can absorb heat energy from the heat source before melting or solidifying, while their temperature remains constant during the phase change. Their storage ability overcomes the difficulty of conducting heat to high ambient temperatures, which can be dissipated later in more temperate conditions. Example of PCMs include, but are not limited to, Sodium Hydrogen Phosphate, Ethylene Glycol, Thermasorb® and Ice and are available in custom-shaped pouches and/or containers suitable for incorporation within a 'PCD'.

According to one embodiment, the phase change used for PCMs is the solid-liquid change. In another embodiment, liquid-gas PCMs are may be used for thermal storage. While liquid-gas PCMs have a high heat of transformation, the increase in volume during the phase change from liquid to gas would be accounted for in the system design according to such embodiments. Other common PCMs that may be used in accordance with various embodiments of the present invention include, but are not limited to, salt hydrides, fatty acids and esters, and various paraffins (such as octadecane).

When PCMs reach the temperature at which they change phase, e.g., their melting point, they absorb large amounts of heat without getting hotter. When the ambient temperature in the space around the PCM material drops, the PCM solidifies, releasing its stored latent heat. As such, PCMs absorb and emit heat while maintaining a nearly constant temperature.

According to one embodiment, phase change material 1740 is stored in a small container. In another embodiment, the container storing PCM 1740 may be divided into multiple cells. In one embodiment, the packaging material used to hold the PCM insulates the PCM from the environment, while permitting the heat from the system to enter the PCM. The packaging material used to hold the PCM may also be durable enough to withstand frequent changes in the storage material's volume as phase changes occur. Additionally, in some embodiments, the packaging material may restrict the passage of water through the walls, so the materials will not dry out. In some embodiments, the packaging must also resist leakage and corrosion. Examples of common PCM packaging materials include, but are not limited to, steel, polyethylene materials, and/or other thermoplastic materials.

One embodiment of the present invention provides that when external TECs 1745 are no longer able to dissipate heat to heat sink 1760, due to high ambient temperature, for example, the adjacent TEC will be activated to dissipate heat to phase change material 1740 for lateral disposal.

According to some embodiments, fans may be used to aid in the dissipation of heat from heat sink 1760. However, the use of traditional fans to aid the dissipation of heat from the heat sinks may involve unreliability and noise when used with garment mounted 'PCDs'. In one embodiment, piezoelectric resonant fan 1730 maybe used. Piezoelectric resonant fan 1730 is a solid-state device with a flexible blade, typically made of mylar, that is set in motion by a piezoceramic bending element. This bending process functions due to an ultra low power oscillating current of electricity determined by fan control unit 1765. The electric field causes the piezoceramic element to elongate, which bends the blade back and forth. This high-amplitude resonant vibration, or 'rapid flapping action' is much like that of a humming bird's wing. Within a 'PCD', piezoelectric fan 1730 may create a large amount of cooling capacity adjacent to an aerodynamic heat sink 1760. Piezoelectric resonant fan 1730 may be enclosed in a duct casing configured to direct airflow into a fan duct, as indicated by arrows 1770, and out across heat sink 1760, as indicated by arrows 1775.

Various embodiments of the present invention may use electronic controls and switching technology. For example, according to one embodiment, an electronic circuit board with an IC chip and micro-switching may be responsible for power management of the 'PCD' system. This system enables the DC current to the 'PCD' to be controlled through Power Width Modulation (PWM) in order to set short term 'duty cycles', which may achieve the desired temperature differential. These cycles may be adjusted as a function of ambient temperature, user preference through thermostatic controls, garment material, garment function, and/or the like . The circuit board may be dedicated to the 'PCD' or be shared with other systems, as for example in a cell phone. In some embodiments, the power source may be shared with other systems such as night vision goggles in a combat helmet.

In some embodiments, a portable power source may used. For example, fuel cells such as high capacity batteries may be used. In some embodiments, portable, lightweight solar power, wind power, self-winding mechanical designs, and/or the like may be used to recharge a portable power source or provide power to the PCD directly. For example, in one embodiment, a primary (disposable) batteries may be considered for some applications. In one embodiment, a 'PCD' will utilize high capacity re-chargeable cells. Examples of battery technology which may be used in accordance with one or more embodiments of the present invention include, but are not limited to, nickel-cadmium (NiCd), nickel metal hydride (NiMH), lithium-ion (Li-Ion) cells and/or the like. Additionally, new battery, or fuel cell, technology which will be developed may be used in accordance with various embodiments of the present invention. For example, the introduction of nano-sized and sub-micron-sized lithium titanium oxide electrodes may give the existing lithium-ion batteries three times their power and greatly reduced re-charge times. Current advances have been accompanied by the introduction of phosphate based cathode materials, which have overcome earlier tendencies towards instability within lithium-ion technology.

In one embodiment, a battery or other power source may be selected to be ultra lightweight and to have a prolonged life. For example, 3.5 volt nickel metal hydride batteries or the very latest lightweight (~21 g) 3.7 volt lithium polymer high capacity re-chargeable batteries may be used with various embodiments of the present invention, which, depending upon the set pulse pattern, provide up to 10 hours or more of continuous pulsed operation. The length of operation supplied by the battery or other power source may depend on one or more factors such as pulse patterns, number of batteries, capacity of the power source, temperature, and/or the like.

In some embodiments, a TEC may have normal operating temperature of between −2° C. (28° F.) and 8° C. (47° F.) depending on the ambient operating temperature. Empirical research has indicated that in order to increase the comfort of the users, thermoelectrically induced 'cold spots' may be pulsed, according to one embodiment of the present invention. As such, instead of a user receiving the normal operating temperature of between −2° C. (28° F.) and 8° C. (47° F.), a more moderate temperature may be provided. In one embodiment, a set of feedback control electronics may be provided to provide a surface temperature of approximately 10-15 degrees below the surface temperature of the skin. In one embodiment, such an effect is created by using a PWM technique and using temperature sensing devices configured to determine the temperature of the user's skin and the temperature of the PCD. In one embodiment, the temperature may be regulated by adjusting the current to the TEC. According to some embodiments, a thermostatic control unit may be provided in which the user may adjust the desired temperature.

It has been further noted that when the temperature of the 'hot face' of a 17 couple TEC module rises to 15° C. (60° F.) above the ambient air temperature, the heat pump action may experience a decline in efficiency and may result in a 'back flow' to the cold face. This potential may be monitored, controlled and avoided within a PCD installation in order to achieve effective cooling under any conceivable climatic condition. In one embodiment, a pulse width modulated TEC may be used to prevent the back flow to the cold surface while preventing the temperature from becoming too cool.

Overall, conventional thermoelectric coolers (TECs) have changed little in a generation due to their relatively small manufactured volume worldwide. A resulting lack of development, until recently, has meant that the devices have operated at only 30% efficiency, therefore requiring additional electrical current to drive them. Various embodiments of the present invention help remove some of the deficiencies and improve the TEC technology. The latest generation of TECs and thermoelectric film are more efficient and battery technology is advancing rapidly. These advances have been significant in overcoming the problems of removing heat from highly insulated environments.

The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A helmet for personal heat control, the helmet comprising:
one or more thermoelectric cooling units configured to rest in a first location in proximity with a user of the helmet, the one or more thermoelectric cooling units comprising:
one or more cooling surfaces configured to receive heat from the user;
one or more heating surfaces thermally insulated from the one or more cooling surfaces; and
one or more heat transfer units configured to transfer the heat from the one or more cooling surfaces to the one or more heating surfaces;
a heat pipe thermally coupled with the one or more heating surfaces and configured to transfer the heat from the first location to a second location in proximity with the helmet, wherein the heat pipe is flexible;
a direct current power source affixed to the helmet and electrically coupled to the one or more thermoelectric cooling units;
an impact-resistant outer shell; and
one or more impact-dampening foam pads affixed to an inside of the impact-resistant outer shell and configured to rest on the user's head,
wherein the one or more thermoelectric cooling units are spaced to avoid interference with the one or more impact-dampening foam pads and configured to rest in proximity with the user's head;
wherein the one or more heat transfer units is a heat sink configured to dissipate heat from the one or more thermoelectric cooling units;
wherein the heat pipe is a plurality of heat pipes, wherein each of the plurality of heat pipes is thermally coupled at one end to the one or more thermoelectric cooling units and thermally coupled at another end to the heat sink, wherein the plurality of heat pipes is configured to transfer heat from the one or more thermoelectric cooling units to the heat sink with minimal conduction heat loss, wherein the plurality of heat pipes is spaced to avoid interference with the plurality of impact-dampening foam pads.

2. The helmet of claim 1, wherein the heat sink is thermally coupled with the heat pipe at the second location.

3. The helmet of claim 2, further comprising a piezoelectric resonant fan configured to draw air over the heat sink.

4. The helmet of claim 2, further comprising a phase change material thermally coupled with the heat pipe at the second location.

5. The helmet of claim 3, wherein the heat pipe extends outside the helmet to an accoutrement, and wherein the heat sink and the piezoelectric resonant fan are situated within the accoutrement.

6. The helmet of claim 1, wherein the direct current power source is flexible.

7. The helmet of claim 1, wherein the direct current power source is a rechargeable battery.

8. The helmet of claim 2, wherein the heat sink is fluted.

9. The helmet of claim 1, further comprising one or more devices selected from the group consisting of: a timer, a solid-state electronic timing switch, and an electroluminescence device.

10. The helmet of claim 1, wherein the helmet is selected from a group consisting of: space helmets, hard hats, construction helmets, welding masks, motor racing helmets, motor cycle helmets, bicycle helmets, football helmets, batting helmets, cricket batting helmets, baseball batting helmets, softball helmets, skiing helmets, riding helmets, equestrian riding helmets, fencing masks, military equipment hats, and military helmets.

11. The helmet of claim 1, further comprising a programmable logic device, wherein the programmable logic device is configured to turn the one or more thermoelectric cooling units on or off based on an expected heat generation pattern.

12. The helmet of claim 11, wherein the programmable logic device is configured via external radio control.

13. The helmet of claim 1, wherein the one or more thermoelectric cooling units is a plurality of thermoelectric cooling units, the helmet further comprising a programmable logic device, wherein the programmable logic device is configured to pulse each of the plurality of thermoelectric units on and off in a predetermined pattern.

14. The helmet of claim 1, further comprising a spreader thermally coupled with at least one of the one or more cooling surfaces.

15. The helmet of claim 1, wherein the one or more thermoelectric cooling units are thermoelectric film.

16. The helmet of claim 1, further comprising a phase change material thermally coupled to at least one of the plurality of heat pipes.

17. The helmet of claim 1, further comprising a piezoelectric resonant fan configured to move air over the heat sink.

18. The helmet of claim 1, further comprising an elasticized band attached at each end to the inside of the impact-resistant outer shell and configured to hold the one or more thermoelectric cooling units against the user's head.

19. The helmet of claim 1, further comprising a halo attached to an outside of the impact-resistant outer shell and configured to house the heat sink.

20. The helmet of claim 1, wherein the heat sink is thermally coupled with at least one of the one or more heat pipes via an additional thermoelectric cooling unit configured to transfer the heat from the at least one of the plurality of heat pipes to the heat sink.

21. The helmet of claim 1, wherein the one or more thermoelectric cooling units includes a first thermoelectric cooling unit and a second thermoelectric cooling unit, wherein the one or more cooling surfaces includes a first cooling surface and a second cooling surface, wherein the one or more heating surfaces includes a first heating surface and a second heating surface, wherein the one or more heat transfer units includes a heat sink,
the first thermoelectric cooling unit comprising:
the first cooling surface configured to rest in proximity with the user's head;
the first heating surface thermally insulated from the first cooling surface;
the heat pipe thermally coupled with the first heating surface and configured to transfer heat away from the first heating surface through the heat pipe;
the second thermoelectric cooling unit comprising:
the second cooling surface thermally coupled with the heat pipe and configured to receive the heat from the first heating surface;
the second heating surface thermally insulated from the second cooling surface; and
the heat sink thermally coupled with the second heating surface and configured to dissipate heat from the second heating surface.

* * * * *